United States Patent
Lum et al.

(10) Patent No.: US 10,420,758 B2
(45) Date of Patent: Sep. 24, 2019

(54) INDOLINYL-SULFONAMIDE INHIBITORS OF TANKYRASE AND METHODS OF USE THEREOF

(71) Applicant: The Board of Regents of the University of Texas System, Austin, TX (US)

(72) Inventors: Lawrence Lum, Dallas, TX (US); Chuo Chen, Dallas, TX (US); Xuewu Zhang, Irving, TX (US); Ozlem Kulak, Dallas, TX (US); Xiaofeng Wu, Grapevine, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 15/571,240

(22) PCT Filed: May 2, 2016

(86) PCT No.: PCT/US2016/030364
§ 371 (c)(1),
(2) Date: Nov. 1, 2017

(87) PCT Pub. No.: WO2016/179066
PCT Pub. Date: Nov. 10, 2016

(65) Prior Publication Data
US 2018/0271848 A1    Sep. 27, 2018

Related U.S. Application Data

(60) Provisional application No. 62/156,260, filed on May 2, 2015.

(51) Int. Cl.
*A61K 31/454* (2006.01)
*A61K 45/06* (2006.01)

(52) U.S. Cl.
CPC ............ *A61K 31/454* (2013.01); *A61K 45/06* (2013.01)

(58) Field of Classification Search
None
See application file for complete search history.

(56) References Cited

U.S. PATENT DOCUMENTS

2014/0038922 A1    2/2014    Lum et al.

FOREIGN PATENT DOCUMENTS

WO    WO 2013/169631    1/2014

OTHER PUBLICATIONS

Chen et al., "Small molecule-mediated disruption of Wnt-dependent signaling in tissue regeneration and cancer," *Nat. Chem. Biol.*, 5:100-107 2009.
Chen et al., "Suppression of PPN/MG61 attenuates Wnt/β-catenin signaling pathway and induces apoptosis in human lung cancer," *Oncogene*, 27:3483-3488, 2008.
Dodge and Lum, "Drugging the cancer stem cell compartment: lessons learned from the hedgehog and Wnt signal transduction pathways," *Annu. Rev. Pharmacol. Toxicol.*, 51:289-310, 2011.
Gunaydin et al., "Novel binding mode of a potent and selective tankyrase inhibitor," *PLoS ONE*, 7:e33740, 2012.
Huang and He, "Wnt/β-catenin signaling: new (and old) players and new insights," *Curr. Opin. Cell Biol.*, 20(2):119-125, 2008.
Huang et al., "Tankyrase inhibition stabilizes axin and antagonizes Wnt signaling," *Nature*, 461:614-620, 2009.
International Preliminary Report on Patentability issued in corresponding International Application No. PCT/US2016/030364, dated Nov. 16, 2017.
International Search Report and Written Opinion issued in corresponding International Application No. PCT/US2016/030364, dated Aug. 4, 2016.
Lum and Clevers, "Cell biology. The unusual case of Porcupine," *Science*, 337:922-923, 2012.
Narwal et al., "Structural basis of selective inhibition of human tankyrases," *J. Med. Chem.*, 55:1360-1367, 2012.
PubChem CID 46247186, pp. 1-10, created Jul. 21, 2010.
Tian et al. "XAV939 promotes apoptosis in a neuroblastoma cell line via telomere shortening," *Oncology Reports*, 32:1999-2006, 2014.
Tian et al., "XAV939, a tankyrase 1 inhibitor, promotes cell apoptosis in neuroblastoma cell lines by inhibiting Wnt/beta-catenin signaling pathway," *J. Exp. Clin. Cancer Res.*, 32:1-9, 2013.
Wahlberg et al., "Family-wide chemical profiling and structural analysis of PARP and tankyrase inhibitors," *Nature Biotechnol.*, 30:283-288, 2012.

*Primary Examiner* — Brian J Davis
(74) *Attorney, Agent, or Firm* — Parker Highlander PLLC

(57) ABSTRACT

The present disclosure provides compounds that may be useful for inhibiting the Tankyrase enzyme. In some aspects, these compounds are useful in the treatment of a disease or disorder related to the misregulation of Tankyrase enzyme such as cancer, degenerative diseases, or fibrotic diseases. Also provided herein are compounds may also be used to prevent the elongation of the telomere in a cell.

17 Claims, 7 Drawing Sheets
Specification includes a Sequence Listing.

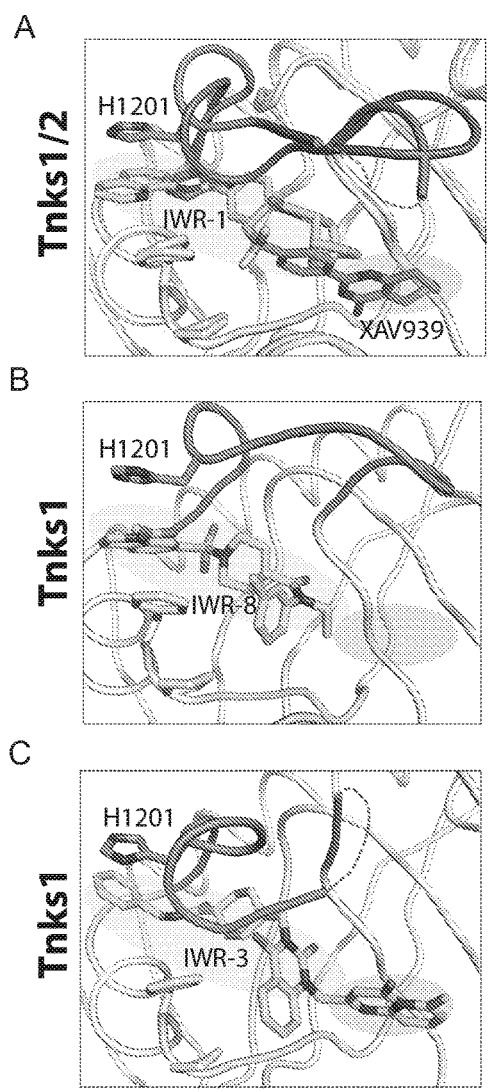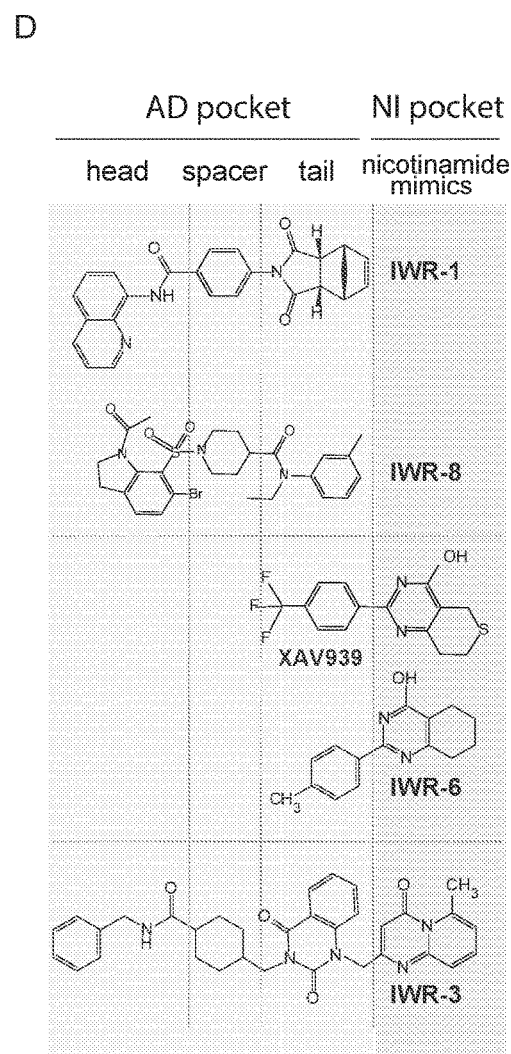
FIGS. 3A-3D

| Cellular product | Starting material | Porcn or Tnks inhibitor | Reference |
|---|---|---|---|
| Dopaminergic neurons | human epidermal neural crest stem cells | IWP-4 | Narytnyk et al. Stem Cell Rev. 2014 Apr;10(2):316-26. |
| Cortical neuroepithelium | mES cells | IWP-4 | Nasu et al. PLoS One. 2012;7(12):e53024. |
| Retinal ganglion cells | hiPS cells | IWR-1 | Tanaka et al. Sci Rep. 2015 Feb 10;5:8344. |
| Retinal neural epithelium | hES cells | IWR-1 | Nakano et al. Cell Stem Cell. 2012 Jun 14;10(6):771-85. |
| Corneal epithelium | hiPS cells | IWR-1 | Mikhailova et al. Stem Cell Reports. 2014 Feb 6;2(2):219-31. |
| Cardiomyocytes | hiPS cells | IWR-1/IWP-1 | Ren et al. J Mol Cell Cardiol. 2011 Sep;51(3):280-7 |
| | hES cells | IWP-2/IWP-4 | Lian et al. Proc Natl Acad Sci U S A. 2012 Jul 3;109(27):E1848-57 |
| | human skeletal muscle derived stem cells | IWR-1 | Tchou et al. Sci Rep. 2014 Oct 14;4:6614. |
| Alveolar epithelial cells | hiPS cells | IWR-1 | Ghaedi et al. J Clin Invest. 2013 Nov;123(11):4950-62. |
| | hES cells | IWP-2 | Huang et al. Nat Biotechnol. 2014 Jan;32(1):84-91. |
| Chondrocytes | mesenchymal stem cells | IWP-2 | Narcisi et al. Stem Cell Reports Mar 10 4(3) 459-72 2015 |

FIG. 7

SEQUENCE LISTING

```
<160> NUMBER OF SEQ ID NOS: 5

<210> SEQ ID NO 1
<211> LENGTH: 19
<212> TYPE: DNA
<213> ORGANISM: Artificial Sequence
<220> FEATURE:
<223> OTHER INFORMATION: Synthetic primer

<400> SEQUENCE: 1
ccacaccctt ctccaatcc                                                   19

<210> SEQ ID NO 2
<211> LENGTH: 20
<212> TYPE: DNA
<213> ORGANISM: Artificial Sequence
<220> FEATURE:
<223> OTHER INFORMATION: Synthetic primer

<400> SEQUENCE: 2
tgccagtttc tttggctctt                                                  20

<210> SEQ ID NO 3
<211> LENGTH: 21
<212> TYPE: DNA
<213> ORGANISM: Artificial Sequence
<220> FEATURE:
<223> OTHER INFORMATION: Synthetic primer

<400> SEQUENCE: 3
ggatgcagaa ggagatcact g                                                21

<210> SEQ ID NO 4
<211> LENGTH: 20
<212> TYPE: DNA
<213> ORGANISM: Artificial Sequence
<220> FEATURE:
<223> OTHER INFORMATION: Synthetic primer
```

```
<400> SEQUENCE: 4
cgatccacac ggagtacttg                                              20

<210> SEQ ID NO 5
<211> LENGTH: 18
<212> TYPE: DNA
<213> ORGANISM: Artificial Sequence
<220> FEATURE:
<223> OTHER INFORMATION: Synthetic primer

<400> SEQUENCE: 5
aatccgtcga gcagagtt                                                18
```

INDOLINYL-SULFONAMIDE INHIBITORS OF TANKYRASE AND METHODS OF USE THEREOF

This application is a national phase application under 35 U.S.C. § 371 of International Application No. PCT/US2016/030364, filed May 2, 2016, which claims the benefit of U.S. Provisional Patent Application No. 62/156,260, filed May 2, 2015, the entirety of each of which is incorporated herein by reference.

This invention was made with government support under grant number 1R01CA168761-01A1, awarded by the National Institutes of Health. The government has certain rights in the invention.

BACKGROUND OF THE INVENTION

1. Field of the Invention

The present invention generally relates to the fields of molecular biology and medicine. More particularly, the present disclosure provides compounds useful as inhibitors of a PARP enzymes such as tankyrase.

2. Description of Related Art

Tankyrase proteins (Tnks1 and 2) belong to the super-family of poly ADP-ribose polymerases (PARPs) that catalyze the addition of poly ADP-ribose onto substrates thereby influencing the activity and stability of the modified proteins (Lehito, et al., 2013; Riffell, et al., 2012). Tnks proteins are expressed in nearly every tissue and control a broad range of cellular processes that include DNA damage repair, Wnt signaling, and telomere length maintenance (Riffell, et al., 2012; Cook, et al., 2002; Smith, et al., 1998). Deletion of both TNKS genes results in embryonic lethality thus revealing redundant but essential roles during development (Chiang, et al., 2008).

In Wnt signaling, Tnks enzymes establish a cellular threshold of response to ligands by controlling the abundance of Axin, a protein that promotes the destruction of the transcriptional co-activator β-catenin (Huang, et al., 2009). Thus, loss of Tnks activity results in accelerated destruction of β-catenin and loss of Wnt-dependent transcriptional responses mediated by the TCF/LEF family of DNA binding proteins. The tumor suppressor Adenomatous polyposis coli (APC) scaffolds a destruction complex that promotes β-catenin turnover and is mutated in >80% of colorectal cancer (CRC) cases. The sensitivity of β-catenin turnover to Tnks activity even in the absence of normal APC function suggests that Tnks inhibitors could be useful against CRC (Huang, et al., 2009; Dodge and Lum, 2011).

Despite the abundance of evidence that disabling Tnks activity can achieve specific anti-Wnt/β-catenin signaling effects (Huang, et al., 2009; Dodge and Lum, 2011), the consequences stemming from Tnks inhibition on other Tnks-associated cellular processes remain unclear (Smith, et al., 1998: Chang, et al., 2005; Cho-Park and Steller, 2013; Guettler, et al., 2011; Ozaki, et al., 2012). Indeed, Tnks1 was initially identified as a regulator of telomeric repeat binding factor (Terf1/Trf1), a member of a protein family now recognized as essential to telomere replication (Hayashi, et al., 2012; Sarek, et al., 2015; Zimmerman, et al., 2014). At the same time, disruption of Tnks function has been shown to induce telomere cohesion (Kim and Smith, 2014). Thus, new compounds which inhibit PARP enzymes such as tankyrase are needed.

SUMMARY OF THE INVENTION

The present disclosure generally provides compounds and their use as PARP inhibitors. In some aspects, these compounds may be used to prevent elongation of telomeres, the differentiation of a stem cell, or in the treatment of a disease or disorder associate with the misregulation of a PARP enzyme such as tankyrase.

In some aspects, the present disclosure provides methods of inhibiting a Tankyrase enzyme in a cell comprising administering to the cell an amount sufficient to cause inhibition of a compound of the formula:

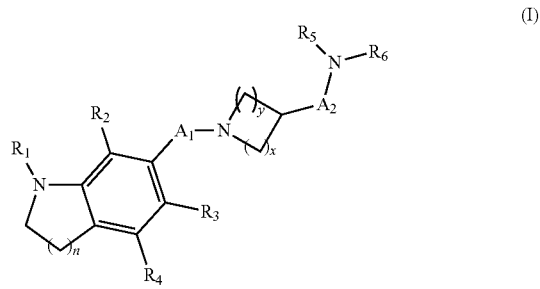

(I)

wherein:
- $R_1$ is hydrogen, alkyl$_{(C\leq 8)}$, substituted alkyl$_{(C\leq 8)}$, acyl$_{(C\leq 8)}$, or substituted acyl$_{(C\leq 8)}$;
- $R_2$, $R_3$, and $R_4$ are each independently selected from hydrogen, amino, cyano, halo, hydroxy, nitro, alkyl$_{(C\leq 8)}$, substituted alkyl$_{(C\leq 8)}$, alkoxy$_{(C\leq 8)}$, substituted alkoxy$_{(C\leq 8)}$, alkylamino$_{(C\leq 8)}$, substituted alkylamino$_{(C\leq 8)}$, dialkylamino$_{(C\leq 8)}$, substitute dialkylamino$_{(C\leq 8)}$, amido$_{(C\leq 8)}$, substituted amido$_{(C\leq 8)}$, acyl$_{(C\leq 8)}$, or substituted acyl$_{(C\leq 8)}$;
- n is 1, 2, 3, or 4;
- $A_1$ and $A_2$ are each independently selected from —C(O)— or —S(O)$_2$—;
- x and y are each independently selected from 1, 2, 3, 4, or 5;
- $R_5$ is hydrogen, alkyl$_{(C\leq 8)}$, substituted alkyl$_{(C\leq 8)}$, acyl$_{(C\leq 8)}$, or substituted acyl$_{(C\leq 8)}$;
- $R_6$ is aryl$_{(C\leq 12)}$, heteroaryl$_{(C\leq 12)}$, or a substituted version of either of these groups;

or a pharmaceutically acceptable salt thereof.

In some embodiments, $R_1$ is acyl$_{(C\leq 8)}$ or substituted acyl$_{(C\leq 8)}$. In some embodiments, n is 1 or 2. In some embodiments, $R_2$ is halo. In some embodiments, x and y are 1 or 2. In some embodiments, $R_5$ is alkyl$_{(C\leq 8)}$ or substituted alkyl$_{(C\leq 8)}$. In some embodiments, $R_6$ is aryl$_{(C\leq 12)}$ or substituted aryl$_{(C\leq 12)}$ such as $R_6$ is tolyl. In some embodiments, $R_6$ is 3-methylphenyl. In some embodiments, the compound is further defined as:

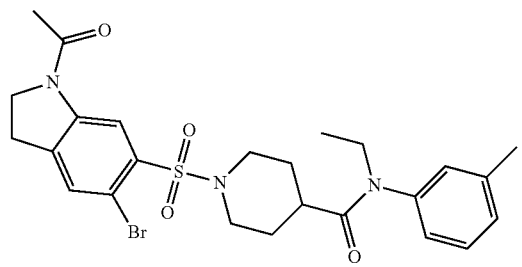 [SMILES: CCN(C(=O)C1CCN(S(=O)(=O)c2cc3c(cc2Br)CCN3C(C)=O)CC1)c1cccc(C)c1]

or a pharmaceutically acceptable salt thereof. In some embodiments, the method is performed in vitro. In other embodiments, the method is performed in vivo. The Tankyrase enzyme may be Tankyrase 1. In other embodiments, the Tankyrase enzyme may be Tankyrase 2. The methods may also further comprise adding one or more additional inhibitors of a Tankyrase enzyme. In some embodiments, the method comprise reducing the activity of a Tankyrase enzyme by more than 50%, by more than 60%, by more than 70%, or by more than 80%. In some embodiments, the method modulates the activity of a telomeric repeat binding factor which may result in shortened telomeres.

In yet another aspect, the present disclosure provides methods of treating a disease or disorder associated with the misregulation of a Tankyrase enzyme in a patient comprising administering to the patient in need thereof a therapeutically effective amount of a compound or a pharmaceutical composition comprising a compound of the formula:

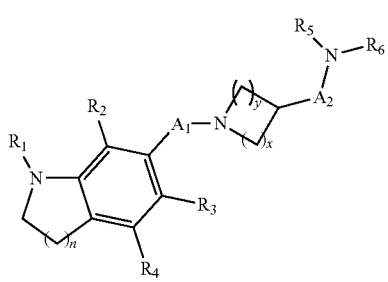

(I)

wherein:
$R_1$ is hydrogen, $alkyl_{(C\leq 8)}$, substituted $alkyl_{(C\leq 8)}$, $acyl_{(C\leq 8)}$, or substituted $acyl_{(C\leq 8)}$;
$R_2$, $R_3$, and $R_4$ are each independently selected from hydrogen, amino, cyano, halo, hydroxy, nitro, $alkyl_{(C\leq 8)}$, substituted $alkyl_{(C\leq 8)}$, $alkoxy_{(C\leq 8)}$, substituted $alkoxy_{(C\leq 8)}$, $alkylamino_{(C\leq 8)}$, substituted $alkylamino_{(C\leq 8)}$, $dialkylamino_{(C\leq 8)}$, substitute $dialkylamino_{(C\leq 8)}$, $amido_{(C\leq 8)}$, substituted $amido_{(C\leq 8)}$, $acyl_{(C\leq 8)}$, or substituted $acyl_{(C\leq 8)}$;
n is 1, 2, 3, or 4;
$A_1$ and $A_2$ are each independently selected from —C(O)— or —S(O)$_2$—;
x and y are each independently selected from 1, 2, 3, 4, or 5;
$R_5$ is hydrogen, $alkyl_{(C\leq 8)}$, substituted $alkyl_{(C\leq 8)}$, $acyl_{(C\leq 8)}$, or substituted $acyl_{(C\leq 8)}$;
$R_6$ is $aryl_{(C\leq 12)}$, $heteroaryl_{(C\leq 12)}$, or a substituted version of either of these groups;
or a pharmaceutically acceptable salt thereof.

In some embodiments, $R_1$ is $acyl_{(C\leq 8)}$ or substituted $acyl_{(C\leq 8)}$. In some embodiments, n is 1 or 2. In some embodiments, $R_2$ is halo. In some embodiments, x and y are 1 or 2. In some embodiments, $R_5$ is $alkyl_{(C\leq 8)}$ or substituted $alkyl_{(C\leq 8)}$. In some embodiments, $R_6$ is $aryl_{(C\leq 12)}$ or substituted $aryl_{(C\leq 12)}$ such as $R_6$ is tolyl. In some embodiments, $R_6$ is 3-methylphenyl. In some embodiments, the compound is further defined as:

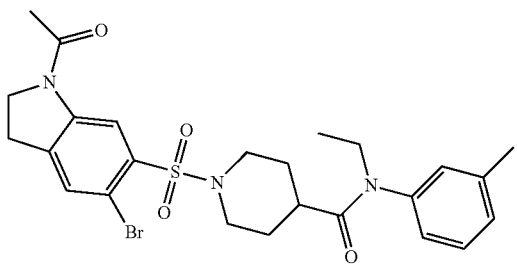 [SMILES: CCN(C(=O)C1CCN(S(=O)(=O)c2cc3c(cc2Br)CCN3C(C)=O)CC1)c1cccc(C)c1]

or a pharmaceutically acceptable salt thereof. In some embodiments, the disease or disorder is cancer. The cancer may be colorectal cancer, chronic lymphocytic leukemia, melanoma, glioma, breast cancer, liver cancer, lung cancer, prostate cancer, pancreatic cancer, bladder cancer, or acute myeloid leukemia. In some embodiments, the cancer is colorectal cancer. In other embodiments, the cancer is acute myeloid leukemia. The methods may also further comprise administering the compound in conjunction with one or more additional cancer therapies. In some embodiments, the additional cancer therapies are another chemotherapeutic compound, radiation therapy, immunotherapy, hormone therapy, toxin therapy, or gene therapy. In other embodiments, the disease or disorder is fibrosis related to aging, non-congenital forms of idiopathic pulmonary fibrosis, or post-injury response to myocardial infarction, skeletal muscle damage, liver damage, lung damage, nerve damage, or kidney dialysis or damage. In other embodiments, the disease or disorder is degenerative disorder. The degenerative disorder may also be osteopetrosis or other disorders associated with increased bone mass, proliferative retinopathy, macular degeneration, arthritis, corneal dystrophies, and Parkinson's disease or other neurodegenerative diseases. In some embodiments, the degenerative disease is treated in vivo. In other embodiments, the degenerative disease is treated by the engrafting of new cells generated in vitro. In some embodiments, the compound is administered: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctivally, subcutaneously, sublingually, topically, transbuccally, transdermally, vaginally, in crèmes, in lipid compositions, via a catheter, via a lavage, via continuous infusion, via infusion, via inhalation, via injection, via local delivery, or via localized perfusion.

In still yet another aspect, the present disclosure provides methods of inducing differentiation of a precursor cell into a mature cell comprising administering to the precursor cell an effective amount of a compound of the formula:

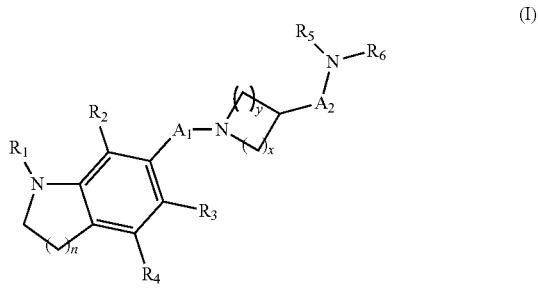

(I)

wherein:
$R_1$ is hydrogen, $alkyl_{(C\leq 8)}$, substituted $alkyl_{(C\leq 8)}$, $acyl_{(C\leq 8)}$, or substituted $acyl_{(C\leq 8)}$;
$R_2$, $R_3$, and $R_4$ are each independently selected from hydrogen, amino, cyano, halo, hydroxy, nitro, $alkyl_{(C\leq 8)}$, substituted $alkyl_{(C\leq 8)}$, $alkoxy_{(C\leq 8)}$, substituted $alkoxy_{(C\leq 8)}$, $alkylamino_{(C\leq 8)}$, substituted $alkylamino_{(C\leq 8)}$, $dialkylamino_{(C\leq 8)}$, substitute dialkylamino$_{(C\leq 8)}$, amido$_{(C\leq 8)}$, substituted amido$_{(C\leq 8)}$, acyl$_{(C\leq 8)}$, or substituted acyl$_{(C\leq 8)}$;

n is 1, 2, 3, or 4;

$A_1$ and $A_2$ are each independently selected from —C(O)— or —S(O)$_2$—;

x and y are each independently selected from 1, 2, 3, 4, or 5;

$R_5$ is hydrogen, alkyl$_{(C\leq 8)}$, substituted alkyl$_{(C\leq 8)}$, acyl$_{(C\leq 8)}$, or substituted acyl$_{(C\leq 8)}$;

$R_6$ is aryl$_{(C\leq 12)}$, heteroaryl$_{(C\leq 12)}$, or a substituted version of either of these groups;

or a pharmaceutically acceptable salt thereof.

In some embodiments, $R_1$ is acyl$_{(C\leq 8)}$ or substituted acyl$_{(C\leq 8)}$. In some embodiments, n is 1 or 2. In some embodiments, $R_2$ is halo. In some embodiments, x and y are 1 or 2. In some embodiments, $R_5$ is alkyl$_{(C\leq 8)}$ or substituted alkyl$_{(C\leq 8)}$. In some embodiments, $R_6$ is aryl$_{(C\leq 12)}$ or substituted aryl$_{(C\leq 12)}$ such as $R_6$ is tolyl. In some embodiments, $R_6$ is 3-methylphenyl. In some embodiments, the compound is further defined as:

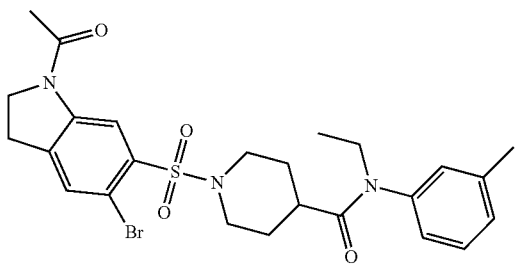 [SMILES: CCN(C(=O)C1CCN(S(=O)(=O)c2cc3c(cc2Br)CCN3C(C)=O)CC1)c1cccc(C)c1]

or a pharmaceutically acceptable salt thereof. In some embodiments, the precursor cell is a stem cell such as an embryonic stem cell or an induced pluripotent stem cell. In some embodiments, the mature cell is a cardiomyocyte, a dopamine producing neuron, a cortical neuron, an retinal ganglion cell, a chondrocyte, a corneal epithelial cell, pneumocyte, or an aveolar epithelial lung cell. In some embodiments, the mature cell is a cardiomyocyte. In other embodiments, the mature cell is a dopaminergic neuron. In other embodiments, the mature cell is a pneumocyte. In other embodiments, the mature cell is a retinal pigment epithelium cell. In some embodiments, the mature cells form a tissue. The tissue may be a cardiac tissue, a neuronal tissue, a lung tissue, cartilage, or an ocular tissue. In some embodiments, the method is performed in vitro. In other embodiments, the cells are incubated with the compound.

In still yet another aspect, the present disclosure provides methods of inhibiting the elongation of telomeres in a cell comprising administering to the cell an effective amount of a compound of the formula:

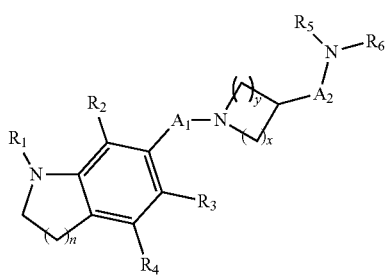

(I)

wherein:

$R_1$ is hydrogen, alkyl$_{(C\leq 8)}$, substituted alkyl$_{(C\leq 8)}$, acyl$_{(C\leq 8)}$, or substituted acyl$_{(C\leq 8)}$;

$R_2$, $R_3$, and $R_4$ are each independently selected from hydrogen, amino, cyano, halo, hydroxy, nitro, alkyl$_{(C\leq 8)}$, substituted alkyl$_{(C\leq 8)}$, alkoxy$_{(C\leq 8)}$, substituted alkoxy$_{(C\leq 8)}$, alkylamino$_{(C\leq 8)}$, substituted alkylamino$_{(C\leq 8)}$, dialkylamino$_{(C\leq 8)}$, substitute dialkylamino$_{(C\leq 8)}$, amido$_{(C\leq 8)}$, substituted amido$_{(C\leq 8)}$, acyl$_{(C\leq 8)}$, or substituted acyl$_{(C\leq 8)}$;

n is 1, 2, 3, or 4;

$A_1$ and $A_2$ are each independently selected from —C(O)— or —S(O)$_2$—;

x and y are each independently selected from 1, 2, 3, 4, or 5;

$R_5$ is hydrogen, alkyl$_{(C\leq 8)}$, substituted alkyl$_{(C\leq 8)}$, acyl$_{(C\leq 8)}$, or substituted acyl$_{(C\leq 8)}$;

$R_6$ is aryl$_{(C\leq 12)}$, heteroaryl$_{(C\leq 12)}$, or a substituted version of either of these groups;

or a pharmaceutically acceptable salt thereof.

In some embodiments, $R_1$ is acyl$_{(C\leq 8)}$ or substituted acyl$_{(C\leq 8)}$. In some embodiments, n is 1 or 2. In some embodiments, $R_2$ is halo. In some embodiments, x and y are 1 or 2. In some embodiments, $R_5$ is alkyl$_{(C\leq 8)}$ or substituted alkyl$_{(C\leq 8)}$. In some embodiments, $R_6$ is aryl$_{(C\leq 12)}$ or substituted aryl$_{(C\leq 12)}$ such as $R_6$ is tolyl. In some embodiments, $R_6$ is 3-methylphenyl. In some embodiments, the compound is further defined as:

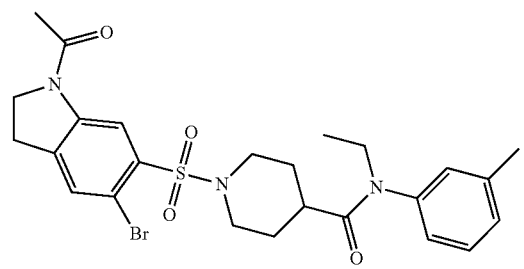 [SMILES: CCN(C(=O)C1CCN(S(=O)(=O)c2cc3c(cc2Br)CCN3C(C)=O)CC1)c1cccc(C)c1]

or a pharmaceutically acceptable salt thereof. In some embodiments, the method is performed in vitro. In other embodiments, the method is performed in vivo. In some embodiments, the methods comprise modulating the activity of a telomeric repeat binding factor. In some embodiments, the compounds increase the binding of a telomeric repeat binding factor to a telomere repeat sequence. In some embodiments, the methods lead to a decrease in telomere length. In some embodiments, the decreased length of the telomeres results in increased cellular apoptosis. The method may be used to treat cancer such as colorectal cancer, chronic lymphocytic leukemia, melanoma, glioma, breast cancer, liver cancer, lung cancer, prostate cancer, pancreatic cancer, bladder cancer, or acute myeloid leukemia. In some embodiments, the cancer is colorectal cancer. In other embodiments, the cancer is acute myeloid leukemia.

In yet another aspect, the present disclosure provides pharmaceutical compositions comprising an excipient or a pharmaceutically acceptable carrier and a compound of the formula:

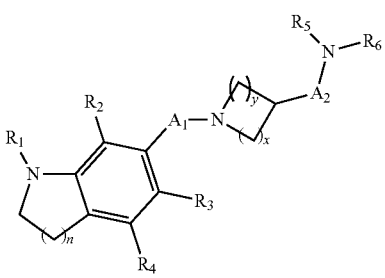

(I)

wherein:
R₁ is hydrogen, alkyl$_{(C≤8)}$, substituted alkyl$_{(C≤8)}$, acyl$_{(C≤8)}$, or substituted acyl$_{(C≤8)}$;
R₂, R₃, and R₄ are each independently selected from hydrogen, amino, cyano, halo, hydroxy, nitro, alkyl$_{(C≤8)}$, substituted alkyl$_{(C≤8)}$, alkoxy$_{(C≤8)}$, substituted alkoxy$_{(C≤8)}$, alkylamino$_{(C≤8)}$, substituted alkylamino$_{(C≤8)}$, dialkylamino$_{(C≤8)}$, substitute dialkylamino$_{(C≤8)}$, amido$_{(C≤8)}$, substituted amido$_{(C≤8)}$, acyl$_{(C≤8)}$, or substituted acyl$_{(C≤8)}$;
n is 1, 2, 3, or 4;
A₁ and A₂ are each independently selected from —C(O)— or —S(O)₂—;
x and y are each independently selected from 1, 2, 3, 4, or 5;
R₅ is hydrogen, alkyl$_{(C≤8)}$, substituted alkyl$_{(C≤8)}$, acyl$_{(C≤8)}$, or substituted acyl$_{(C≤8)}$;
R₆ is aryl$_{(C≤12)}$, heteroaryl$_{(C≤12)}$, or a substituted version of either of these groups;
or a pharmaceutically acceptable salt thereof.

In some embodiments, R₁ is acyl$_{(C≤8)}$ or substituted acyl$_{(C≤8)}$. In some embodiments, n is 1 or 2. In some embodiments, R₂ is halo. In some embodiments, x and y are 1 or 2. In some embodiments, R₅ is alkyl$_{(C≤8)}$ or substituted alkyl$_{(C≤8)}$. In some embodiments, R₆ is aryl$_{(C≤12)}$ or substituted aryl$_{(C≤12)}$ such as R₆ is tolyl. In some embodiments, R₆ is 3-methylphenyl. In some embodiments, the compound is further defined as:

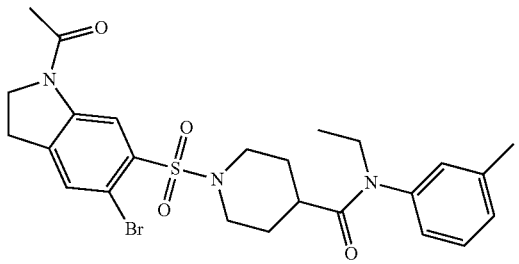 [SMILES: CCN(C(=O)C1CCN(S(=O)(=O)c2cc3c(cc2Br)CCN3C(C)=O)CC1)c1cccc(C)c1]

or a pharmaceutically acceptable salt thereof. In other embodiments, the compound is not a compound of the formula:

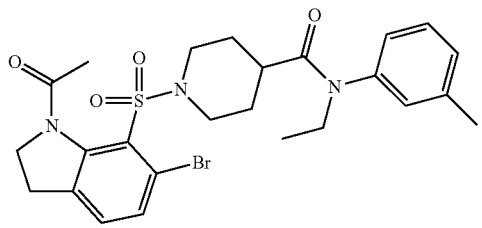 [SMILES: CCN(C(=O)C1CCN(S(=O)(=O)c2c(Br)ccc3c2N(C(C)=O)CC3)CC1)c1cccc(C)c1]

or a pharmaceutically acceptable salt thereof. In some embodiments, the pharmaceutical composition is formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctivally, subcutaneously, sublingually, topically, transbuccally, transdermally, vaginally, in crèmes, in lipid compositions, via a catheter, via a lavage, via continuous infusion, via infusion, via inhalation, via injection, via local delivery, or via localized perfusion.

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1A) Biochemical markers of Tnks inhibition associated with the Wnt/β-catenin pathway. The Tnks inhibitors XAV-939 and IWR-1 induce stabilization of both Tnks enzymes and Axin proteins in SW480 cells (expressing truncated Apc protein) but promote destruction of β-catenin (β-cat). (FIG. 1B) A biochemical screen to identify additional Tnks inhibitors from the IWR collection of Wnt pathway inhibitors. The effects of the IWR compounds on Tnks 1 and 2, β-catenin, and acetylated tubulin (Ac-Tub; loading control) expression levels were determined in SW480 cells by Western blot analysis. IWR-1 to -2 are known Tnks inhibitors whereas IWR-3 to -5 were previously shown to induce β-cat destruction but not assigned as Tnks inhibitors. Novel compounds that induced changes in Tnks and β-catenin levels identified by this screen were re-named IWR-6 to -8 (in bold). (FIG. 1C) Chemotype-based grouping of potential Tnks inhibitors identified from the IWR collection. IWR-6 and -7 are similar to the previously reported XAV-939 compound.

(FIG. 2A) IWR-3, -6 and -8 directly target Tnks. Representative IWRs from each chemotype were evaluated for their ability to inhibit purified recombinant Tnks1 protein (Tnks1 SAM-AARP protein). Parsylation of immobilized histone protein was determined by colorimetric detection of incorporated biotinylated NAD+ in 96 well format. (FIG. 2B) IWR-8 inhibits β-catenin activity induced by loss of APC function. EC$_{50}$ of IWR-8 as well as IWR-1, IWR-6, and IWR-8 were measured in DLD-1 cells using a Wnt/β-catenin specific luciferase reporter. (FIG. 2C) IWR-8 inhibits cell growth in a cancer cell line with compromised APC function. SW403 cells previously shown to exhibit Wnt/β-catenin pathway-dependent cell growth in culture (Scholer-Dahirel, et al., 2011) were treated with either IWR-3, IWR-8, or IWP-2 (an inhibitor of the Wnt acyltransferase Porcupine (Chen, et al., 2009); a negative control).

FIGS. 3A-3D show crystallographic studies reveal distinct modes of chemical attack by members of the IWR collection of Tnks inhibitors. (FIG. 3A) Crystal structure of IWR-1/Tnks1. The structure of XAV-939, a prototypical PARP inhibitor, bound to Tnks2 (PDB ID: 3KR$_8$) is superimposed for comparison with respect to chemical binding pocket preference and ability to induce conformational change in the D-loop. (FIG. 3B) Crystal structure of IWR-8/Tnks1. (FIG. 3C) Crystal structure of IWR-3/Tnks1. The D-loop of Tnks1 (1196-1211) or Tnks2 (1043-1058) is shown in turquoise and cyan, respectively. His1201 which interacts with all three IWR compounds and facilitates chemical-specific D-loop conformational changes is highlighted. Adenosine (AD) and nicotinamide (NI) binding sites are shown in the crystal structure as light gray and dark gray, respectively. (FIG. 3D) Summary of binding pocket preference of IWR compounds that target Tnks enzymes. Given the structural similarity of IWR-6 and -7 to XAV-939, these novel molecules likely engage the NI pocket of Tnks.

(FIG. 4A) Porcn inhibitors afford a Tnks-independent approach to disrupting Wnt/β-catenin signaling. Chemicals targeting the Wnt acyltransferase Porcn abrogate Wnt palmitoylation which in turn results in loss of activity of the Frizzled (Fzd) family of Wnt receptors. Fzd receptors directly induce activation of the cytoplasmic signaling molecule Dishevelled (Dvl) in a ligand-dependent manner, which in turn results in activation of β-catenin and transcription mediated by the TCF family of DNA binding proteins. IWP-2 and the clinical candidate LGK-974 represent two structurally distinct Porcn inhibitors. (FIG. 4B) Tnks but not Porcn inhibitors induce DNA damage at telomeres. The appearance of co-localized Terf2 and pH2A.X (an indicator of DNA damage at the telomere ends; Telomere Induced Foci or TIFs) was scored using indirect immunofluorescence in Hela cells (expressing wild-type Apc protein). (FIG. 4C) Quantification of results represented in "B". Cells with >5 TIFs were scored as positive for telomeric damage (left bars). Mean total phosphorylated H2A.X (γ H2A.X) was used to measure general DNA damage responses (right bars). (FIG. 4D) Tnks and Porcn inhibitors disrupt β-catenin-dependent transcription in HeLa cells. qPCR analysis of Axin2, a target gene of Wnt/β-catenin signaling, reveals both classes exert influence on β-catenin activity. (FIG. 4E) IWP-2 and LGK-974 but not Tnks inhibitors block ligand-dependent phosphorylation of Dvl2, a cytoplasmic signaling molecule regulated by the Frizzled family of Wnt receptors. (FIG. 4F) IWR compounds do not inhibit telomerase. Digital droplet-based telomerase extension analysis of genomic DNA isolated from HeLa cells treated for 24 hrs with indicated compounds.

(FIG. 5A) Strategy for isolating HeLa cells transfected with Tnks1 and/or Tnks2 siRNAs. A plasmid supporting constitutive expression of GFP is co-transfected with a pool of siRNAs (4 individual siRNAs per gene) targeting either Tnks1 or Tnks2 or both into HeLa cells. GFP+ HeLa cells isolated by flow cytometry were analyzed for levels of TIFs 24 hrs later. (FIG. 5B) Biochemical evidence for on-target effects of Tnks siRNA pools in GFP+ HeLa cells. GFP+ cells presumably harboring indicated Tnks siRNA pools were isolated by FAC sorting then subjected to Western blot analysis following culturing in the presence/absence of IWR-1 for 24 hrs. IWR-1 is used here to aid in the visualization of relative Tnks protein abundance in siRNA treated/untreated cells. (FIG. 5C) Quantification of TIFs in GFP+ HeLa cells transfected with indicated siRNA pools as described above (left bars). Mean total phosphorylated H2A.X (γ H2A.X) was used to measure general DNA damage responses (right bars). (FIG. 5D) IWR-1, -3, and -6 inhibits Tnks-mediated parsylation of Terf1 in vitro. Tnks1-Fc fusion protein purified using protein A sepharose from HEK293 cells transiently transfected with Tnks1-Fc DNA was incubated with recombinant Terf1-GST protein, NAD-Biotin (2.5 μM), and indicated compounds (5 μM). (FIG. 5E) Tnks inhibitors increase Terf1 binding to telomeric repeat sequences. HEK293 cells transfected with a hTerf1-myc or control DNA were treated with indicated compounds for 36 hrs prior to lysing. Lysate was incubated with biotinylated oligos containing 5× copies of Terf1-binding or mutated telomeric repeat sequence and streptavidin-coated sepharose. Starting material and oligo-bound protein were subjected to Western blot analysis.

(FIG. 6A) IWR-1, IWR-8, and IWR-6 induce telomere shortening. HeLa cells were incubated with IWR-1, IWR-8, or IWP-6 at various concentrations for the indicated number of population doublings (PD) and telomere length measured by terminal restriction fragment (TRF) analysis. Density of radioprobe hybridization relative to the vertical distance from the largest molecular weight marker was quantified using ImageJ and the point of highest density in each lane marked by a dark line. Position of control telomere restricted fragment signal is indicated with dotted line. Lanes with insufficient strength in labeling or that were disrupted with blemishes during experimental processing were not quantified. (FIG. 6B) Inhibition of β-catenin transcriptional does not induce telomere shortening. The same assay described in "A" was used to test the Porcn inhibitor IWP-2. (FIG. 6C) Model of Tnks-dependent regulation of Wnt/β-catenin transcriptional and telomere length maintenance in human cells. Excessive Terf1 binding to DNA in the absence of Tnks-mediated Terf1 parsylation results in replication fork stalling in telomeres (Munoz, et al., 2009; Ohki and Ishikawa, 2004) which then presumably results in telomere shortening.

FIG. 7 shows a summary of cell engineering achievements using the IWP and IWR classes of Porcn and Tnks inhibitors, respectively. mES cells=mouse embryonic stem cells; hES cells=human embryonic stem cells; hiPS cells=human induced pluripotent stem cells.

DESCRIPTION OF ILLUSTRATIVE EMBODIMENTS

Figures 1A, 1B, 1C:
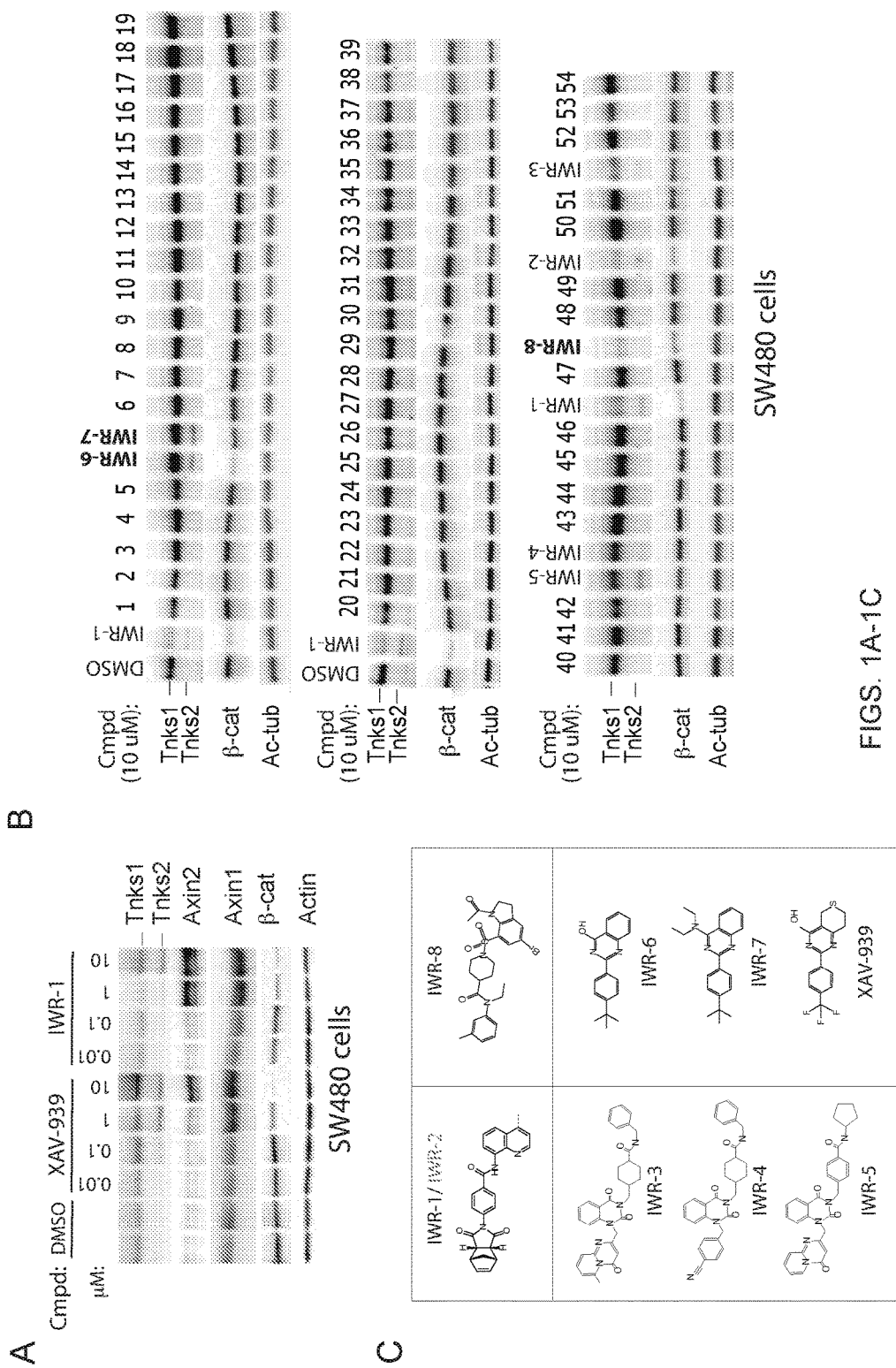
FIGS. 1A-1C show the identification of novel Tnks inhibitors from the IWR chemical collection.

The present disclosure provides one or more compound which may be used to inhibit tankyrase or other PARP enzymes. These compounds may be used to treat one or more diseases which are associated with a misregulation of these protein enzymes. In some embodiments, the diseases and disorders associated with misregulation of PARP enzymes and particular Tankyrase enzymes include but are not limited to cancer, degenerative diseases such as neurodegenerative disorders, or diseases associated with fibrosis. In some aspects of the present disclosure, the compounds may be used to prevent the elongation of telomeres within a cell and thus increase cellular apoptosis.

I. The Wnt Signal Transduction Pathways and Tankyrase Enzymes

The Wnt gene family encodes secreted ligand proteins that serve key roles in differentiation and development. This family comprises at least 15 vertebrate and invertebrate genes including the *Drosophila* segment polarity gene wingless and one of its vertebrate se homologues, integrated from which the Wnt name derives. As noted above, the Wnt proteins appear to facilitate a number of developmental and homeostatic processes.

The Wnt signalling pathways comprises a number of proteins involved in the transduction of cellular responses to secreted Wnt/wingless signalling proteins. Wnt proteins that control "non-canonical" pathways, such as the Wnt/calcium and planar cell polarity pathways, induce cellular responses that are not dependent upon β-catenin. In the Wnt/β-catenin pathway, the Frizzled receptor then activates Disheveled protein, which blocks the inhibiting action of Zeste-white-3 kinase (or GSK3β in vertebrates, Glycogen Synthase Kinase-3β) upon the Armadillo protein (a β-catenin protein). The β-catenin protein transduces the Wnt signal from the cytoplasm to the nucleus. In the absence of Wnt signalling, β-catenin is constitutively degraded by the proteasome and can be found in a multimeric complex with conductin (or axin), APC (Adenomatous Polyposis Coli) and GSK3β. APC mediates the binding of β-catenin to conductin and serves to activate the conductin protein. Conductin acts as a scaffold to assemble the components of the degradation pathway of β-catenin. GSK3β, a serine/threonine kinase, phosphorylates β-catenin, thus stimulating its degradation by the proteasome.

Upon Wnt signalling, GSK3β kinase is inactivated, leading to stabilization of the β-catenin protein. β-Catenin is then released from the multimeric complex and translocates into the nucleus. Once in the nucleus, β-catenin interacts with the LEF/TCF (Lymphoid Enhancer Factor/T-Cell Factor) family of HMG (High Mobility Group) box transcription factors. The LEF/TCF factors are stimulated through interaction with β-catenin to become potent transactivators of a number of genes including c-myc and cyclin D1.

It has recently been found that β-catenin degradation can be promoted by stablising Axin through the inhibition of the poly-ADP-ribose polymerase (PARP) enzymes tankyrase 1 and tankyrase 2, as described in WO 2009/059994 and Huang et al., (Huang, 2009). Both tankyraseisoforms interact with a highly conserved domain of Axin and stimulate its degradation through the ubiquitin-proteasome pathway. This previously unknown mechanism for stabilising Axin protein, thereby enhancing β-catenin degradation, can be exploited for treating Wnt signaling-related disorders. Axin proteins are essential regulators of a spectrum of physiological processes, including brain oligodendrocyte progenitor cell differentiation for remyelination (Fancy, 2011), and epithelial-to-mesenchymal transition during pulmonary fibrosis (Ulsamer, 2012). Thus, by way of stabilizing Axin proteins, Tankyrase inhibitors may be used as a therapy for remyelination post brain injury and pulmonary fibrosis.

Tankyrase has several binding protein partners, including TRF1, a double-stranded telomeric repeat binding protein (Smith, 1998); NuMA, an essential protein in mitotic spindle assembly (Chang, 2005); IRAP, an integral membrane protein involved in glucose uptake in response to insulin (Chi, 2000); and Mcl-1, a pro-apoptotic protein (Bae, 2003).

By way of its various interacting proteins, tankyrase proteins have been implicated in different biological functions. Tankyrase poly (ADP-ribosyl)ates TRF1, releasing it from telomeres and enhancing telomere access to telomerase. Thus, tankyrase functions as a positive regulator for telomere elongation by telomerase, supported by the findings that long-term overexpression of tankyrase leads to telomere elongation (Cook, 2002). Telomere maintenance by telomerase has been attributed to the uncontrolled proliferation of cancer cells (Hahn, 1999). Tankyrase may be useful as a therapeutic target for cancer therapy by inhibiting the telomere accessibility for telomerase. Tankyrase inhibition could be used as an effective cancer therapy to treat patients with a wide spectrum of cancers, including leukemia, lymphoma, multiple myeloma, lung, and breast cancer.

Tankyrase also plays a role in cell mitosis by: 1) poly (ADP-ribosyl)ating NuMA during mitosis and regulating its functions at spindle poles (Chang, 2005); 2) by regulating spindle assembly and structure (Chang, 2004); and 3) by maintaining sister chromatid resolution at telomeres (Dynek, 2004). Inhibition of tankyrase leads to cell mitotic arrest or senescence, and thus could be exploited for treating diseases that have abnormal mitotic division, such as cancer. Examples include breast, colon, lung, ovarian, leukemia, lymphoma, and melanoma. In addition, tankyrase 1 was identified as a gene required for centrosome clustering, a mechanism that cancer cells with supernumerary centrosomes employs to suppress multipolar mitosis and enable bipolar mitosis (Kwon, 2008). Thus inhibition of tankyrase may be used to treat cancers through centrosome amplification, including both solid and haematological cancers, examples include breast, bladder, lung, colon, and leukemia.

Moreover, one of the cellular localizations of tankyrase is at the Golgi apparatus co-localizing with the glucose transporter GLUT4 vesicles where tankyrase is associated with IRAP, and tankyrase is implicated in the regulation of GLUT4 trafficking in adipocytes (Chi, 2000).Tankyrase-deficient mice exhibit reduced adiposity and increased energy expenditure by increases in both fatty acid oxidation and insulin-stimulated glucose utilization (Yeh, 2009). This supports tankyrase involvement in energy homeostasis in mammals and inhibiting tankyrase can be exploited for treating metabolic diseases, such as obesity.

II. Therapeutic Implications of Wnt-Controlled Signal Transduction Pathways

A. Tumors

As noted above, evidence suggests that targeting the Wnt-mediated signal transduction pathways would be therapeutically useful in a broad range of diseases (Barker and Clevers, 2006) (Veeman et al, 2003). Aged mice or mice that exhibit premature stem cell senescence that are treated with extracellular protein inhibitors of Wnt pathways exhibit improved regenerative capacity in various tissues (Brack et al., 2007; Liu et al., 2007). Mutations leading to constitutive activation of the Wnt pathway are critical events in a variety of human cancers including colon cancer, melanoma, hepatocellular carcinoma and others. The end result of constitutive activation of the Wnt/β-catenin pathway is a dramatic increase in the level of β-catenin protein in the cytoplasm. Inappropriate stabilization of β-catenin, leading to increased levels of the protein, can be caused by mutations in a variety of proteins in the Wnt signalling pathway.

Blockade of the Wnt/β-catenin pathway in a variety of cancers using either genetic or chemical approaches been shown to abrogate aberrant cell growth (Barker and Clevers, 2006). Furthermore, inhibition of this pathway may directly influence the cells that sustain cancer cell growth and enable metastasis, and that are thought to be resistant to traditional chemotherapeutic agents (Ailles and Weissman, 2007).

Aberrant Wnt-mediated pathway responses, sustained by genetic changes that result either in altered Wnt ligand activity or in altered functioning of pathway regulators, have been associated with a broad range of cancers. See Clevers, 2006 and Polakis, 2007, both of which are incorporated herein by reference. Notably, more than 90% of colorectal cancer (CRC) tumors harbor a loss-of-function mutation in APC, a suppressor of the Wnt/β-catenin pathway. See Sjoblom et al., 2006, which is incorporated herein by reference. The ability of IWR compounds to stabilize Axin proteins and induce β-catenin destruction even in the absence of normal APC protein function suggests that they may block aberrant cell growth supported by hyperactivation of Wnt/β-catenin responses.

Indeed, IWR compounds are able to inhibit aberrant Wnt/β-catenin activity as a consequence of Apc loss in both mouse L cells (using Apc small interfering RNAs) and DLD-1 colorectal cancer cells (that harbor a loss-of-function mutation in APC). The ability of IWR-3 to mimic the cell growth effects of β-catenin siRNAs in several cancer cell lines that exhibit differences in growth dependency on Wnt/β-catenin pathway activity was also tested. Notably, IWR-3 mimicked the effects of β-catenin siRNAs on the growth of cells derived from cancers of the colon (DLD-1) and prostate (DU145) but not lung (H460), which suggests that IWR-3 successfully targeted the Wnt/β-catenin pathway in these cells. Indeed, overexpression of β-catenin can overcome the effects of IWR-3 on DLD-1 cell growth.

Aberrant transcriptional induction of Wnt/β-catenin target genes is typically observed in CRC cells that harbor loss-of-function mutations in the APC tumor suppressor. Consistent with the ability of IWR compounds to inhibit cancerous Wnt/β-catenin pathway responses, a decrease in the expression of Axin2 in DLD-1 cells after exposure to IWR-1 for 2 h was observed. Thus, Axin protein stability can be chemically controlled in order to suppress cancerous Wnt/β-catenin activity, as demonstrated by IWR compounds. See Chen et al. (2007), which is incorporated herein by reference.

The reliance of certain cancer types on Wnt pathways for sustaining growth likely represents an exploitation of normal tissue maintenance cues provided by Wnt proteins. For example, loss in activity of the tumor suppressor and β-catenin inhibitor Apc heightens Wnt signaling in a tissue that is well established to rely on Wnt signals for homeostatic renewal. Similarly, β-catenin mutations are frequently found in cancers of the liver, a tissue that relies on Wnt signaling for regeneration (The Cancer Genome Network, 2012). Given the frequency of mutations that give rise to a truncated Apc protein observed in colorectal cancer (~90%), the discussion and development of agents targeting Wnt signaling have largely focused on disabling pathway components that regulate the β-catenin transcriptional apparatus. The prevalence of APC mutations suggests that these lesions arise early in the course of disease progression (Fearon and Vogelson, 1990; Barker, et al., 2009). At the same time, deregulated growth control in the gut epithelium is observed when APC is mutated in putative stem cells but not in differentiated cells thus providing compelling evidence that the cell of origin in gut cancers are likely stem cells (Cadigan and Waterman, 2012). Thus, cancer cells of origin must exhibit greater sensitivity than gut stem cells to loss of Wnt signaling in order for anti-Wnt agents to be viable disease management tools for this disease.

Whereas cancer genome sequencing has assigned Wnt signaling to various cancers based on the prevalence of mutations in Wnt pathway components, other cancers such as acute myeloid leukemia (AML) that have shown sensitivity to Wnt pathway modulation in animal models are devoid of such mutations (Lian, et al., 2013). Given our understanding of Wnt signaling in cancer has been predominantly informed by studies in the gut, the existence of these other cancers either reflects our partial inventory of Wnt signaling components in other cell types or the limitations of genomic sequencing for revealing epigenetic changes in Wnt signaling such as altered RNA splicing or histone methylation. Either Porcn or β-catenin targeting agents or both could be useful in these disease contexts.

B. Regeneration

In addition to the applications of Wnt inhibitors as anti-cancer agents, these molecules may also be used for influencing cell differentiation programs in vitro. Indeed, two classes of Porcn and Tnks inhibitors have been widely adopted for use in the production of medically useful cell types from various precursor cells including induced pluripotent stem cells (iPSCs) (FIG. 7). When used in combination with other small molecules that influence cell fate outcome and in different cell culture conditions, nearly homogenous cell products can be achieved in some cases with these Wnt pathway antagonists (Narytnyk, et al., 2014; Ren, et al., 2011). For example, a chemically based strategy for cardiomyocyte production from iPSCs entails the use of two chemicals—one compound to activate Wnt signaling (GSK3β inhibitor) under embryoid body formation conditions and a Porcn inhibitor (IWP-2 and IWP-4) to inactivate Wnt signaling under monolayer growth conditions (Narytnyk, et al., 2014). In another example, a Tnks inhibitor could substitute for a Porcn inhibitor thus demonstrating the necessity of on-target effects of these Wnt inhibitors for robust cardiomyocyte induction (Nakano, et al., 2012).

The production of cardiomyocytes from iPSCs using only chemical reagents targeting the Wnt/β-catenin pathway has not only confirmed the well-recognized prowess of Wnt signaling in cell fate determination processes but also galvanized efforts to deploy Wnt pathway modulators in other tissue engineering agendas (see FIG. 7). Other successes include the production of dopaminergic neurons and retinal pigmented epithelial cells which could be used for in vitro screening for molecules with biological activity in these cell types or for the replacement of prematurely degenerated cells (Ren, et al., 2011; Distler, et al., 2013). The availability of these agents and the ease with which they can be applied to cultured cells has helped fuel the rapid growth in their use for tissue engineering. With the successful production of therapeutically relevant cell types, a challenge in the future will be to improve the integration of these cells into the host, a process that could be facilitated by stemming fibrotic responses in injured or aged tissues with the use of Wnt inhibitors with favorable pharmacokinetic properties (Henderson, et al., 2010; Wang, et al., 2014; Rouleau, et al., 2010).

In some embodiments of the present disclosure, pluripotent stem cells and neural stem cells are exposed in vitro or in vivo to a compound described herein, resulting in the differentiation of the stem cells into neural precursor cells, neurons, or another type of cell such as a cardiac cell, a lung cell, a bone cell, or a cell from the eye. A neural precursor cell is a cell that can generate neuronal cells (i.e. neurons or neuronal precursors) and glial cells (i.e., astrocytes, oligodendrocytes, or glial cell precursors), but cannot give rise to a pluripotent or neural stem cell.

The pervasive influence of the Wnt proteins in tissue homeostasis and tumorigenesis suggests areas such as regenerative medicine and anti-cancer therapy may benefit from therapies that target this pathway. Achieving transient repression of pathological Wnt response without incurring permanent damage to normal stem cell function is a key anticancer therapeutic goal. The inventors tested for the ability of zebrafish to resume regenerative processes following a chemically induced blockade of fin regrowth. Fish with resected caudal fins that were bred in water containing IWR-1 for 7 d were able to regenerate tissue to nearly normal levels after chemical removal, which suggests that transient inhibition of Wnt/β-catenin response does not permanently alter the ability of stem cells to self-renew.

In some aspects of the present disclosure, Wnt signals can promote cell proliferation and tissue expansion but also control fate determination or terminal differentiation of postmitotic cells. Sometimes, these disparate events, proliferation and terminal differentiation, can be activated by Wnt in different cell types within the same structure, such as the hair follicle or the intestinal crypt (Reya and Clevers, 2005). Numerous Tcf target genes have been identified in diverse biological systems. These studies tend to focus on target genes involved in cancer, as exemplified by the wide interest in the Wnt target genes cMyc and Cyclin D1.

Patterning of the embryo and cell specification events are activated by a few evolutionarily conserved pathways, one of which is the Wnt/β-catenin pathway. These signaling proteins are used repeatedly during development and in diverse regions. The canonical Wnt pathway has been shown to regulate cell fate decisions, cell proliferation, and cell migration in the embryo. Canonical Wnt signaling is important for neural development, neural crest specification and differentiation, and cardiac development. The signals are transduced in a cell-context dependent manner to result in rapid changes in gene transcription. Thus, in some aspects, the present disclosure provides compounds which can modulate the Wilt signaling pathway and particularly inhibit PARP enzymes such as Tankyrase. These compounds thus may be used to promote neural development and stem cell differentiation.

Reported evidence indicates that canonical Wnt signaling during narrow windows has differential effects during cardiac specification and heart development, Wnt signaling has been shown to be a major regulator of cardiogenesis (Cleutjens et al., 1999; Foley and Mercola, 2005; Salloway, 2003). Prior to gastrulation, Wnt/β-catenin signaling promotes cardiac differentiation whereas signaling during gastrulation inhibits heart formation (Cleutjens et al., 1999; Foley and Mercola, 2005; Salloway, 2003). Consistent with these studies, early treatment of mouse embryonic stem cells with Wnt3a stimulates mesoderm induction whereas late Wnt3a stimulation inhibits cardiac differentiation. Furthermore, the Wnt inhibitors Dickkopf-1 (Dkk-1) and secreted frizzled-related proteins (sFRPs) have been shown to induce cardiac differentiation of stem cells (Cleutjens et al., 1999; Salloway, 2003; Pandur et al., 2002)). Although these studies clearly demonstrate the importance of Wnt signaling in cardiac development, less is known about its role in adult cardiac repair. A recent study using Wnt (axin2-LacZ) reporter mice demonstrated that Wnt signaling is increased post-MI in cardiomyocytes of the border zone and remote area between 7-21 days whereas infiltrating CD45$^+$ inflammatory cells showed Wnt activation between 3-7 days (Oerlemans et al., 2009). Hence, endogenous activation of the Wnt pathway occurs in the heart in cardiomyocytes and other heart cells and is evident just prior to the initiation of the remodeling phase (day 10-26) of murine infarct repair. The inventors hypothesize that infarct-induced Wnt activation contributes to adverse cardiac remodeling, a process that may be averted by Wnt inhibition. Several recent studies support this hypothesis. Transgenic mice in which β-catenin was downregulated in an alpha-MHC-restricted manner (i.e., resulting in lower cardiac Wnt signaling) demonstrated favorable ischemic remodeling (Zelarayàn et al., 2008). Other groups reported functional deterioration after injury in mice expressing a stabilized β-catenin (i.e., activated Wnt signaling) in cardiomyocytes (Malekar et al., 2010; Baurand et al., 2007). Finally, it has been shown that mesenchymal stem cells overexpressing sFRP2, a Wnt inhibitor, reduced cardiomyocyte apoptosis (Mirotsou et al., 2007; Alfaro et al., 2008).

Thus, in one aspect of the present invention, there is provided a method inhibiting pathologic cardiac remodeling with the compounds disclosed herein. The cardiac remodeling may be associated with various aspects of cardiac disease, such as cardiac hypertrophy, dilated cardiomyopathy and heart failure. The treatment would comprise provision of the antibody in any of the aforementioned routes when formulated appropriately for that delivery mode. In particular, intravenous injection (systemic or into the cardiac vasculature) and intracardiac (muscular) injection are envisioned. Repeated treatments (2, 3, 4, 5, 6, 7, 8, 9, 10, 15, 20, 25, 50 or more) over extended periods (24 hrs, 48 hrs, 72 hrs, 1 wk, 2 wk, 3 wk, 4 wk, 1 month, 2 months, 3 months, 4 months, 5 months, 6 months, 1 year or longer) are contemplated.

III. Wnt Protein Signalling Inhibitors

The compounds provided by the present disclosure are shown, for example, above in the summary of the invention section and in the claims below. They may be made using the methods outlined in the Examples section. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

Compounds of the invention may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present invention can have the S or the R configuration.

Chemical formulas used to represent compounds of the invention will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

Compounds of the invention may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

Compounds of the present invention may also exist in prodrug form. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

It will appreciated that many organic compounds can form complexes with solvents in which they are reacted or from which they are precipitated or crystallized. These complexes are known as "solvates." Where the solvent is water, the complex is known as a "hydrate." It will also be appreciated that many organic compounds can exist in more than one solid form, including crystalline and amorphous forms. All solid forms of the compounds provided herein, including any solvates thereof are within the scope of the present invention.

Persons of ordinary skill in the art will be familiar with methods of purifying compounds of the present invention. One of ordinary skill in the art will understand that compounds of the present invention can generally be purified at any step, including the purification of intermediates as well as purification of the final products. In preferred embodiments, purification is performed via silica gel column chromatography or HPLC.

IV. Definitions

As used herein, "Wnt protein signaling pathway" refers to the pathways by which binding of the Wnt protein to extracellular receptors is either translated into the nucleus and results in transcriptional activation of a variety of genes, or otherwise results in biochemical changes that influence cell behavior. The Wnt protein signaling pathways involve a variety of proteins including Frizzled, Disheveled, Axin, APC, GSK3β, β-catenin, LEF/TCF transcription factors, etc. Cells from many different species express homologs of the proteins involved in Wnt protein signalling pathways and accordingly have functionally equivalent Wnt protein signalling pathways. In some aspects of the present disclosure, the compounds are used herein to influence the activity and modulate the Wnt protein signaling pathway by inhibiting the activity of a PARP protein and preferentially inhibiting the activity of the Tankyrase enzyme.

When used in the context of a chemical group: "hydrogen" means —H; "hydroxy" means —OH; "oxo" means =O; "carbonyl" means —C(=O)—; "carboxy" means C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfonyl" means —S(O)$_2$—; "hydroxylsulfonyl" means —SO$_2$OH; "aminosulfonyl" means —SO$_2$NH$_2$ and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "⚌" represents a single bond or a double bond. Thus, for example, the formula

includes

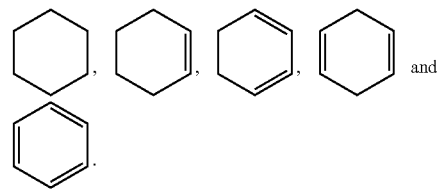

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol "⌇", when drawn perpendicularly across a bond (e.g.,

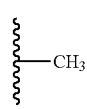

for methyl) indicates a point of attachment of the group. It is noted that the point of attachment is typically only identified in this manner for larger groups in order to assist the reader in unambiguously identifying a point of attachment. The symbol "—" means a single bond where the group attached to the thick end of the wedge is "out of the page." The symbol "⫿⫿⫿⫿" means a single bond where the group attached to the thick end of the wedge is "into the page". The symbol "∼∼∼" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

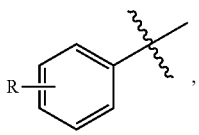

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

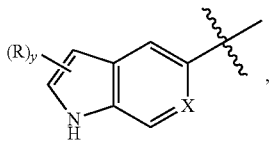

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and compound classes below, the number of carbon atoms in the group is as indicated as follows: "Cn" defines the exact number (n) of carbon atoms in the group/class. "C≤n" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. Compare with "alkoxy$_{(C≤10)}$", which designates alkoxy groups having from 1 to 10 carbon atoms. Also compare "phosphine$_{(C≤10)}$", which designates phosphine groups having from 0 to 10 carbon atoms. "Cn-n'" defines both the minimum (n) and maximum number (n') of carbon atoms in the group. Thus, "alkyl$_{(C2-10)}$" designates those alkyl groups having from 2 to 10 carbon atoms. Typically the carbon number indicator follows the group it modifies, is enclosed with parentheses, and is written entirely in subscript; however, the indicator may also precede the group, or be written without parentheses, without signifying any change in meaning. Thus, the terms "C5 olefin", "C5-olefin", "olefin$_{(C5)}$", and "olefin$_{C5}$" are all synonymous. When any group or compound class below is used with the term "substituted", any carbon atoms of the chemical group replacing the hydrogen atom do not count towards the total carbon atom limit for that group or compound class.

The term "saturated" when used to modify a compound or an atom means the compound or atom has no carbon-carbon double and no carbon-carbon triple bonds, except as noted below. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$-(methylene), —CH$_2$CH$_2$—, —CH$_2$C(CH$_3$)$_2$CH$_2$—, and —CH$_2$CH$_2$CH$_2$— are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the compound H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The following groups are non-limiting examples of substituted alkyl groups: —CH$_2$OH, —CH$_2$Cl, —CF$_3$, —CH₂CN, —CH₂C(O)OH, —CH₂C(O)OCH₃, —CH₂C(O)NH₂, —CH₂C(O)CH₃, —CH₂OCH₃, —CH₂OC(O)CH₃, —CH₂NH₂, —CH₂N(CH₃)₂, and —CH₂CH₂Cl. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —CH₂Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH₂F, —CF₃, and —CH₂CF₃ are non-limiting examples of fluoroalkyl groups.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C₆H₄CH₂CH₃ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

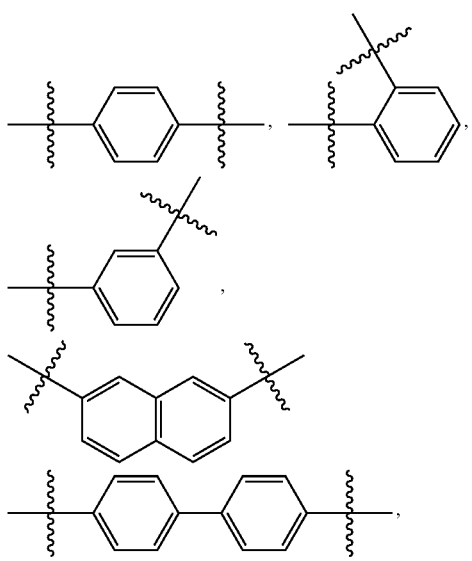

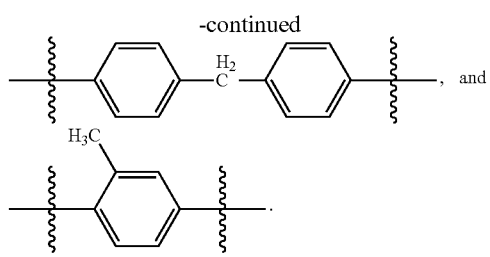

An "arene" refers to the compound H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. A "heteroarene" refers to the compound H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂.

The term "acyl" when used without the "substituted" modifier refers to the group —C(O)R, in which R is a hydrogen, alkyl, cycloalkyl, alkenyl, aryl, aralkyl or heteroaryl, as those terms are defined above. The groups, —CHO, —C(O)CH₃ (acetyl, Ac), —C(O)CH₂CH₃, —C(O)CH₂CH₂CH₃, —C(O)CH(CH₃)₂, —C(O)CH(CH₂)₂, —C(O)C₆H₅, —C(O)C₆H₄CH₃, —C(O)CH₂C₆H₅, —C(O)(imidazolyl) are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkane, as defined above, wherein at least one of the hydrogen atoms has been replaced with a —CHO group. When any of these terms are used with the "substituted" modifier one or more hydrogen atom (including a hydrogen atom directly attached to the carbon atom of the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples include: —OCH$_3$ (methoxy), —OCH$_2$CH$_3$ (ethoxy), —OCH$_2$CH$_2$CH$_3$, —OCH(CH$_3$)$_2$ (isopropoxy), —OC(CH$_3$)$_3$ (tert-butoxy), —OCH(CH$_2$)$_2$, —O-cyclopentyl, and —O-cyclohexyl. The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkylamino" when used without the "substituted" modifier refers to the group —NHR, in which R is an alkyl, as that term is defined above. Non-limiting examples include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$ and —N(CH$_3$)(CH$_2$CH$_3$). The terms "cycloalkylamino", "alkenylamino", "alkynylamino", "arylamino", "aralkylamino", "heteroarylamino", "heterocycloalkylamino", "alkoxyamino", and "alkylsulfonylamino" when used without the "substituted" modifier, refers to groups, defined as —NHR, in which R is cycloalkyl, alkenyl, alkynyl, aryl, aralkyl, heteroaryl, heterocycloalkyl, alkoxy, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. When any of these terms is used with the "substituted" modifier one or more hydrogen atom attached to a carbon atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —NHC(O)OCH$_3$ and —NHC(O)NHCH$_3$ are non-limiting examples of substituted amido groups.

As used herein, a "label" is any composition or moiety detectable by spectroscopic, photochemical, biochemical, immunochemical, or chemical means. Labels that may be employed in the present invention include radioactive labels (e.g., $^{32}$P, $^{125}$I, $^{14}$C, $^{3}$H, and $^{35}$S) and fluorescent dyes (e.g., Cy3). An example of a label that is not directly detected but is detected through the use of indirect methods is biotin.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result.

As used herein, the term "IC$_{50}$" refers to an inhibitory dose which is 50% of the maximum response obtained.

An "isomer" of a first compound is a separate compound in which each molecule contains the same constituent atoms as the first compound, but where the configuration of those atoms in three dimensions differs.

A "neural stem cell" is an undifferentiated cell from neural tissue that is capable of giving rise to more neural stem cells (i.e., exhibits self renewal) and to progeny cells that will terminally differentiate into neural cells. The neural stem cell can be an adult or embryonic neural stem cell.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiary-butylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002), The term "pluripotent stem cell" refers to a cell capable of giving rise to cells of all three germinal layers, that is, endoderm, mesoderm and ectoderm. Although in theory a pluripotent cell can differentiate into any cell of the body, the experimental determination of pluripotency is typically based on differentiation of a pluripotent cell into several cell types of each germinal layer. In some embodiments of the present invention, a pluripotent stem cell is an embryonic stem (ES) cell derived from the inner cell mass of a blastocyst. In other embodiments, the pluripotent stem cell is an induced pluripotent stem cell derived by reprogramming differentiated cells. In some embodiments, the pluripotent stem cell is an embryonic stem cell derived by somatic cell nuclear transfer, "Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Therapeutically effective amount" or "pharmaceutically effective amount" means that amount which, when administered to a subject or patient for treating a disease, is sufficient to effect such treatment for the disease.

The term "therapeutic benefit" or "therapeutically effective" as used throughout this application refers to anything that promotes or enhances the well-being of the subject with respect to the medical treatment of a condition. This includes, but is not limited to, a reduction in the onset, frequency, duration, or severity of the signs or symptoms of a disease. For example, a therapeutically effective amount of a compound of the present invention (that is, a Wnt protein signalling inhibitor) may be an amount sufficient to treat or prevent osteopetrosis.

The terms "inhibiting," or "reducing" or any variation of these terms, when used in the claims and/or the specification, includes any measurable decrease or complete inhibition to achieve a desired result. For example, there may be a decrease of 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, reduction of activity compared to normal. In a further example, following administering of a Wnt protein signalling inhibitor, a cancer patient may experience a reduction in tumor size.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

The terms "contacted" and "exposed," when applied to a cell, are used herein to describe the process by which a compound of the present invention is administered or delivered to a target cell, or are placed in direct juxtaposition with the target cell. The terms "administered" and "delivered" are used interchangeably with "contacted" and "exposed."

As used herein, the term "water soluble" means that the compound dissolves in water at least to the extent of 0.010 mole/liter or is classified as soluble according to literature precedence.

Modifications or derivatives of the compounds, agents, and active ingredients disclosed throughout this specification are contemplated as being useful with the methods and compositions of the present invention. Derivatives may be prepared and the properties of such derivatives may be assayed for their desired properties by any method known to those of skill in the art, such as methods described herein.

Prodrugs and solvates of the compounds of the present invention are also contemplated herein. The term "prodrug," as used herein, is understood as being a compound which, upon administration to a subject, such as a mammal, undergoes chemical conversion by metabolic or chemical processes to yield a compound any of the formulas herein, or a salt and/or solvate thereof. Solvates of the compounds of the present invention are preferably hydrates.

As used herein, "protecting group" refers to a moiety attached to a functional group to prevent an otherwise unwanted reaction of that functional group. The term "functional group" generally refers to how persons of skill in the art classify chemically reactive groups. Examples of functional groups include hydroxyl, amine, sulfhydryl, amide, carboxyl, carbonyl, etc. Protecting groups are well-known to those of skill in the art. Non-limiting exemplary protecting groups fall into categories such as hydroxy protecting groups, amino protecting groups, sulfhydryl protecting groups and carbonyl protecting groups. Such protecting groups may be found in Greene and Wuts, 1999, incorporated herein by reference in its entirety. The Wnt protein signalling inhibitors described herein are also contemplated as protected by one or more protecting groups—that is, the inhibitors are contemplated in their "protected form."

In view of the above definitions, other chemical terms used throughout this application can be easily understood by those of skill in the art. Terms may be used alone or in any combination thereof.

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

V. Pharmaceutical Formulations and Routes for Administration

Pharmaceutical compositions of the present invention comprise an effective amount of one or more candidate substances (e.g., a Wnt protein signalling inhibitor) or additional agents dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one candidate substance or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, pp 1289-1329, 1990). Except insofar as any conventional carrier is incompatible with the active ingredient, its use in the therapeutic or pharmaceutical compositions is contemplated.

The candidate substance may comprise different types of carriers depending on whether it is to be administered in solid, liquid or aerosol form, and whether it needs to be sterile for such routes of administration as injection. Compounds of the present invention may be administered orally, intraadiposally, intraarterially, intraarticularly, intracranially, intradermally, intralesionally, intramuscularly, intranasally, intraocularally, intrapericardially, intraperitoneally, intrapleurally, intraprostaticaly, intrarectally, intrathecally, intratracheally, intratumorally, intraumbilically, intravaginally, intravenously, intravesicularlly, intravitreally, liposomally, locally, mucosally, orally, parenterally, rectally, subconjunctival, subcutaneously, sublingually, topically, transbuccally, transdermally, vaginally, in crèmes, in lipid compositions, via a catheter, via a lavage, via continuous infusion, via infusion, via inhalation, via injection, via local delivery, via localized perfusion, bathing target cells directly, or by other method or any combination of the foregoing as would be known to one of ordinary skill in the art (see, for example, Remington's Pharmaceutical Sciences, 1990). In particular embodiments, the composition may be formulated for oral delivery. Pharmaceutical compositions comprising a compound of the present invention are also contemplated, and such compositions may be adapted for administration via any method known to those of skill in the art, such as the methods described above.

In particular embodiments, the composition is administered to a subject using a drug delivery device. Any drug delivery device is contemplated for use in delivering a pharmaceutically effective amount of a Wnt protein signalling inhibitor.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will typically determine the concentration of active ingredient(s) in a composition and appropriate dose(s) for the individual subject.

The dose can be repeated as needed as determined by those of ordinary skill in the art. Thus, in some embodiments of the methods set forth herein, a single dose is contemplated. In other embodiments, two or more doses are contemplated. Where more than one dose is administered to a subject, the time interval between doses can be any time interval as determined by those of ordinary skill in the art. For example, the time interval between doses may be about 1 hour to about 2 hours, about 2 hours to about 6 hours, about 6 hours to about 10 hours, about 10 hours to about 24 hours, about 1 day to about 2 days, about 1 week to about 2 weeks, or longer, or any time interval derivable within any of these recited ranges.

In certain embodiments, it may be desirable to provide a continuous supply of a pharmaceutical composition to the patient. This could be accomplished by catheterization, followed by continuous administration of the therapeutic agent, for example. The administration could be intra-operative or post-operative.

In certain embodiments, pharmaceutical compositions may comprise, for example, at least about 0.1% of a Wnt protein signalling inhibitor. In other embodiments, the Wnt protein signalling inhibitor may comprise between about 2% to about 75% of the weight of the unit, or between about 25% to about 60%, for example, and any range derivable therein. In other non-limiting examples, a dose may also comprise from about 1 µg/kg/body weight, about 5 µg/kg/body weight, about 10 µg/kg/body weight, about 50 µg/kg/body weight, about 100 µg/kg/body weight, about 200 µg/kg/body weight, about 350 µg/kg/body weight, about 500 µg/kg/body weight, about 1 mg/kg/body weight, about 5 mg/kg/body weight, about 10 mg/kg/body weight, about 50 mg/kg/body weight, about 100 mg/kg/body weight, about 200 mg/kg/body weight, about 350 mg/kg/body weight, about 500 mg/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 µg/kg/body weight to about 500 mg/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal, or combinations thereof.

The Wnt protein signalling inhibitor may be formulated into a composition, such as a pharmaceutical composition, in a free base, neutral, or salt form. Pharmaceutically acceptable salts are described herein.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. It may be preferable to include isotonic agents, such as, for example, sugars, sodium chloride, or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in certain embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the candidate substance is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. In certain embodiments, carriers for oral administration comprise inert diluents (e.g., glucose, lactose, or mannitol), assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain embodiments an oral composition may comprise one or more binders, excipients, disintegration agents, lubricants, flavoring agents, or combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar, or both.

Sterile injectable solutions may be prepared by incorporating a compound of the present invention in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, certain methods of preparation may include vacuum-drying or freeze-drying techniques which yield a powder of the active ingredient plus any additional desired ingredient from a previously sterile-filtered liquid medium thereof. The liquid medium should be suitably buffered if necessary and the liquid diluent (e.g., water) first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition should be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin, or combinations thereof.

VI. Combination Therapy

In order to enhance or increase the effectiveness of a Wnt protein signalling inhibitor of the present invention, the inhibitor may be combined with another therapy, such as another agent that combats and/or prevents cancer, osteopetrosis, a degenerative disease, or type II diabetes. For example, Wnt protein signalling inhibitors of the present invention may be provided in a combined amount with an effective amount another agent that is known to reduce tumor size.

It is contemplated that combination therapy of the present invention may be used in vitro or in vivo. These processes may involve administering the agents at the same time or within a period of time wherein separate administration of the substances produces a desired therapeutic benefit. This may be achieved by contacting the cell, tissue, or organism with a single composition or pharmacological formulation that includes two or more agents, or by contacting the cell with two or more distinct compositions or formulations, wherein one composition includes one agent and the other includes another.

The compounds of the present invention may precede, be co-current with and/or follow the other agents by intervals ranging from minutes to weeks. In embodiments where the agents are applied separately to a cell, tissue or organism, one would generally ensure that a significant period of time did not expire between the time of each delivery, such that the agents would still be able to exert an advantageously combined effect on the cell, tissue or organism. For example, in such instances, it is contemplated that one may contact the cell, tissue or organism with two, three, four or more modalities substantially simultaneously (i.e., within less than about a minute) as the candidate substance. In other aspects, one or more agents may be administered about 1 minute, about 5 minutes, about 10 minutes, about 20 minutes about 30 minutes, about 45 minutes, about 60 minutes, about 2 hours, about 3 hours, about 4 hours, about 5 hours, about 6 hours, about 7 hours about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, about 48 hours, about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 1, about 2, about 3, about 4, about 5, about 6, about 7 or about 8 weeks or more, and any range derivable therein, prior to and/or after administering the candidate substance.

Various combination regimens of the agents may be employed. Non-limiting examples of such combinations are shown below, wherein a PARP inhibitor and specifically a tankyrase inhibitor is "A" and a second agent, such as an anti-cancer agent, is "B":

| A/B/A | B/A/B | B/B/A | A/A/B | A/B/B | B/A/A | A/B/B/B | B/A/B/B |
|---|---|---|---|---|---|---|---|
| B/B/B/A | B/B/A/B | A/A/B/B | A/B/A/B | | | A/B/B/A | B/B/A/A |
| B/A/B/A | B/A/A/B | A/A/A/B | B/A/A/A | | | A/B/A/A | A/A/B/A |

A. Anti-Cancer Therapy

An anti-cancer agent may be used in combination therapy with Wnt protein signalling inhibitors of the present invention. As used herein, an "anti-cancer" agent is capable of negatively affecting cancer in a subject, for example, by killing one or more cancer cells, inducing apoptosis in one or more cancer cells, reducing the growth rate of one or more cancer cells, reducing the incidence or number of metastases, reducing tumor size, inhibiting tumor growth, reducing the blood supply to a tumor or one or more cancer cells, promoting an immune response against one or more cancer cells or a tumor, preventing or inhibiting the progression of a cancer, or increasing the lifespan of a subject with a cancer. Anti-cancer agents are well-known in the art and include, for example, chemotherapy agents (chemotherapy), radiotherapy agents (radiotherapy), a surgical procedure, immune therapy agents (immunotherapy), genetic therapy agents (gene therapy), reoviral therapy, hormonal therapy, other biological agents (biotherapy), and/or alternative therapies. In some embodiments, the present disclosure provides a combination therapy of a compound provided herein with 5-fluorouracil, leucovorin, and oxaliplatin or a compound provided herein with capecitabine and oxaliplatin. These combination therapies may be used in the treatment with colorectal cancer. Also, in some embodiments, the present disclosure provides a combination therapy comprising administering a compound provided herein and is co-administered with cytarabine and an anthracycline drug, such as daunorubicin and idarubicin. In some embodiments, these combination therapies may be administered for the treatment or prevention of acute myeloid leukemia (AML).

B. Osteopetrosis Therapy

Osteopetrosis, also known as marble bone disease and Albers-Schonberg disease, is an extremely rare inherited disorder whereby the bones harden, becoming denser, in contrast to the more prevalent osteomalacia, in which the bones soften. Bone marrow transplant therapy may be combined with administration of Wnt protein signalling inhibitors of the present invention to treat or prevent osteopetrosis. Other treatments targeting osteopetrosis that may be combined with Wnt protein signalling inhibitors described herein include those disclosed in the following documents, each of which is incorporated herein by reference: U.S. Pat. Nos. 7,241,732; 7,186,683; 6,943,151; 6,833,354; 6,699,873; 6,686,148; 5,806,529; 5,777,193; RE35,694; 5,641,747; and 4,843,063.

C. Degenerative Disease Therapy

As discussed herein, degenerative diseases may be treated using Wnt protein signalling inhibitors of the present invention. Accordingly, other treatments that target degenerative diseases may be combined with administration of the Wnt protein signalling inhibitors. Non-limiting examples of degenerative diseases include type II diabetes and age-related impairment of tissue repair.

1. Type II Diabetes Therapy

Type II diabetes is a chronic, progressive disease that has no clearly established cure. It is a metabolic disorder that is primarily characterized by insulin resistance, relative insulin deficiency and hyperglycemia. Treatment options that may be combined with Wnt protein signalling inhibitor administration include exercise, diet management to control the intake of glucose, and use of anti-diabetic drugs (e.g., metformin, phenformin, repaglinide, nateglinide, rosiglitazone, pioglitazone or miglitol).

2. Age-Related Impairment of Tissue Repair Therapy

A variety of tissues degenerate over time as one ages, such as skeletal muscle and organ tissues (e.g., heart, kidney, lung and liver). Wnt protein signalling inhibition has been implicated in, for example, muscle regeneration (Brack et al., 2007). Therapies pertaining to age-related impairment of tissue repair that may be combined with Wnt protein signalling inhibitor administration include, for example, gene therapy, such as described by Barton-Davis et al. (1998; incorporated herein by reference) and drugs described by Lynch (2004; incorporated herein by reference).

VII. Examples

The following examples are included to demonstrate certain preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Materials and Methods

Reagents.

Antibodies were purchased from the following sources: BD Biosciences (Ctnnb1), Sigma (β-Actin and acetylated tubulin), Santa Cruz Biotechnology (Tnks, GST), Cell Signaling Technology (Axin1, Axin2, and Dvl2), Millipore [phospho-Histone H2A.X (Ser139)/gamma H2A.X], and Epitomics (Terf2). HeLa, DLD-1, and SW480 cells were acquired from ATCC. IWR-1 and IWP-2 were synthesized as previously described (Chen, et al., 2009). Sources of chemicals: IWR-3 to -8 (ChemDiv or ChemBridge), XAV-939 (Maybridge) and LGK-974 (ActiveBiochem). See Example 4 for IWR-8 synthesis.

Biochemical Assays.

For Western blot analysis cell lysates were generated with either PBS-NP40 buffer [phosphate-buffered saline (PBS)/1% NP40], or Tris-Triton X-100 buffer [50 mM Tris (pH 8), 200 mM NaCl, 1 mM EDTA, 1% Triton X-100, 10% glycerol, 1 mM DTT, 0.5 mM deoxycholate]. Both buffers were supplemented with protease inhibitor cocktail (Sigma). For telomeric oligonucleotide pull-down assays, cell lysates are generated with Tris-Triton X-100 buffer supplemented with a protease inhibitor cocktail, 5 µM ADP-HPD, and 1 µM of IWR-1 (to prevent Tnks parsylation post-lysis). The lysates were cleared by centrifugation at 15,000 rpm for 10 min. Terf1 is incubated with either biotinylated telomeric $(TTAGGG)_5$ or control $(TGAGGG)_5$ oligonucleotides and streptavidin sepharose for 4 hrs followed by washing with the same buffer.

RNAi and Flow Cytometry.

Control, Tnks1 (Dharmacon MU-004740-01-0002), Tnks2 (Dharmacon MU-004741-01-0002) or Tnks1&2 siRNA pools were co-transfected with a GFP expression construct into HeLa cells using Effectene (Qiagen). After 24 hrs GFP+ cells were sorted with a MoFlo-XDP flow cytometer (Beckman Coulter). ~5000 GFP+ cells were plated on coverslips and incubated for 24 hrs then processed for TIF quantification (see below). For Western blot analysis, ~2500 GFP+ cells were plated in 24 well tissue culture plates and incubated with IWR-1 (10 µM) for 24 hrs prior to cell lysis.

Luciferase Reporter Assays.

Assays were executed as described using a Dual Luciferase kit (Promega), and SuperTopFlash and control SV40-driven Renilla luciferase reporters (SV40-Ren luc) (Chen, et al., 2009).

Telomere Dysfunction Induced Foci (TIF) Assay.

Cells were treated with chemicals for 24 hrs before fixation [2% formaldehyde and permeabilized in 0.5% (v/v) of NP-40], then incubated with gamma H2A.X and Terf2 antibodies and secondary antibodies (mouse fluorescein isothiocyanate—conjugated or Alexa Fluor 488—conjugated antibodies). Primary and secondary antibodies were diluted in PBS, 0.2% fish gelatin, and 0.5% BSA. Cells were imaged using a Zeiss LSM 780 confocal/multiphoton microscope and 3D co-localization assessed using Bitplane Imaris software. The TIF index was determined by assessment of co-localization of pH2A.X and Terf2 for 90-100 cells in 10 random areas within each slide.

Terminal Restriction Fragment (TRF) Telomere Length Assay.

$1\times10^6$ cells were collected and washed with PBS. DNA was isolated using the manufacturer's instructions (Qiagen). 2.5 µg DNA was digested with six different restriction enzymes (HhaI, HinfI, MspI, HaeIII, RsaI, AluI) (New England Biolabs) and incubated at 37° C. overnight. Digested DNA was separated on a 0.7% agarose gel overnight at 70V. The terminal restriction fragment (TRF) gel was denatured for 20 mins in denaturing solution (0.5 M NaOH, 1.5 M NaCl, pH 13.2) and dried on Whatman 3 MM paper under vacuum for 3 hrs at 56° C. The gel was neutralized for 15 mins in neutralization buffer (1.5 M NaCl, 0.5 M Tris-HCl, pH 8.0) and then probed with a radiolabeled telomeric probe (C-rich) for 16 hrs at 42° C. in 5×SSC buffer, 5×Denhardt's solution, 10 mmol/L $Na_2HPO_4$, and 1 mmol/L $Na_2H_2P_2O_7$. The gel was washed once with 2×SSC, 0.1% SDS, twice with 0.5×SSC, 0.1% SDS and then twice with 0.5×SSC, 1% SDS at room temperature for 15 mins. Gels were exposed to a PhosphorImager screen overnight and analyzed using a Typhoon PhosphorImager scanner system (Molecular Dynamics). Radioprobe hybridization density relative to vertical distance was plotted using ImageJ software with an average of 25 data points generated for each lane.

Protein Expression and Purification.

The catalytic domain of human Tnks1 (residues 1105-1313) was expressed by using a modified pET28 vector, which encodes an N-terminal His6-tag and a cleavage site for the Tobacco Etch Virus (TEV) protease. Protein expression was induced by 0.1 mM IPTG at 15° C. when the culture of the bacteria strain BL21 (DE3) transformed with the plasmid reached O.D. of 1.5. Cells were harvested 12 hrs after induction and lysed by Frenchpressing. The lysate was cleared by centrifugation at 15000 rpm for 1 hr. The protein was purified by Ni-NTA-based affinity chromatography and ion exchange chromatography. The N-terminal His6-tag was removed by overnight TEV protease treatment at 4° C. Purified protein was concentrated and stored in −80° C.

Crystallization, Data Collection and Structure Determination.

The purified Tnks1 catalytic domain at 5 mg/mL (0.22 mM) mixed with IWR-1 (the exo-form), IWR-3 and IWR-8 at 0.25 mM were subjected to crystallization trials by using sitting-drop 96-well plates. Following initial hits of crystallization, large crystals were obtained by hanging-drop vapor diffusion in conditions optimized based on the initial conditions. Crystals of the Tnks1/IWR-1 complex were grown at 20° C. in 0.1 M Bis-Tris (pH 5.3), 0.15 M $MgCl_2$ and 20-23% PEG3350. Crystals of the Tnks1/IWR-3 complex were grown at 20° C. in 0.1 M Tris (pH 7.5), 0.2 M sodium acetate and 30% PEG4000. Crystals of the Tnks1/IWR-8 complex were grown at 20° C. in 0.1 M Bis-Tris propane (pH 8.0), 0.2 M sodium bromide and 25% PEG3350. PDB IDs for structures are as follows: Tnks1/IWR-1 (4OA7), Tnks1/IWR-3 (4TOS), and Tnks1/IWR-8 (4TOR).

Crystals were cryo-protected in the crystallization buffer supplemented with 25% glycerol and flash-cooled in liquid nitrogen. Diffraction data were collected at 100K on beamline 19ID at the Advanced Photon Source (Argonne National Laboratory). Data were indexed, integrated and scaled by using HKL2000. The structure of the Tnks1 catalytic domain in the apo state (PDB ID: 2RF5) (Lehito, et al., 2008) was used as the search model for molecular replacement by using the Phaser module in the Phenix package (McCoy, et al., 2007). Iterative model building and refinement were performed by using the Phenix and Coot programs, respectively (Adams, et al., 2002; Emsley and Cowtan, 2004). The IWR compounds were placed when the Rfree was below 32% and the position of the compound was well defined by the electron density map. Comprehensive model validation was performed by using MolProbity (Chen, et al., 2010). Detailed statistics of data collection and refinement are listed in Table 1. Structure figures were rendered in PyMOL (the PyMOL Molecular Graphics System, Schrodinger).

Quantitative PCR.

Total RNA was purified using RNeasy Plus Mini Kit (Qiagen), and reverse transcribed by ProtoScript First Strand cDNA Synthesis Kit (New England Biolabs) according to the manufacturer's protocol. qPCR was performed using FastStart SYBR Green Master (Roche) on a Light Cycler 480 System. Primers used for RT-PCR are as follows:

hAXIN2-F (SEQ ID NO: 1)
ccacaccttctccaatcc

```
-continued
hAXIN2-R                              (SEQ ID NO: 2)
tgccagtttctttggctctt Actin-β-F                             (SEQ ID NO: 3)
ggatgcagaaggagatcactg Actin-β-R                             (SEQ ID NO: 4)
cgatccacacggagtacttg
```

In Vitro Tnks Activity Assays.

The HT Universal Color PARP Assay Kit w/Histone Coated Strip Wells (Trevigen) was used to monitor the activity of purified Tnks1 SAM-PARP protein (1 mg/96 well reaction; provided by Herwig Schüler) according to the manufacturers' protocol. Tnks-Fc construct was generated by PCR-based cloning of human Tnks1 sequence in frame into pcDNA3-hIgG-Fc vector using BglII restriction sites (Lum, et al., 1998). Overexpressed Tnks-Fc protein immobilized on Protein A sepharose was incubated with human Terf1-GST protein (Abnova) and NAD biotin (2.5 µM; Trevigen) for 30 min. at RT prior to Western blot analysis. Parsylated Terf1 protein was detected using streptavidin-HRP. Terf1-GST or Tnks1-Fc proteins were detected by Western blot analysis with anti-GST or anti-Fc antibodies, respectively.

Digital Droplet PCR.

The ddTRAP assay was performed as previously described (Ludlow, et al., 2014). Briefly, pellets of 100,000 fresh sample cells were lysed on ice for 30 mins in NP-40 lysis buffer (10 mM Tris-HCl, at pH 8.0, 1 mM EDTA, 1 mM $MgCl_2$, 1% (vol/vol) NP-40, 0.25 mM sodium deoxycholate, 150 mM NaCl, 10% (vol/vol) glycerol, 5 mM β-mercaptoethanol, 0.1 mM AEBSF [4-(2-aminoethyl)benzenesulfonyl fluoride hydrochloride)]. 1250 cell equivalents of lysate were added to the telomerase extension reaction in TRAP buffer (20 mM Tris-HCl pH 8.3, 1.5 mM $MgCl_2$) with 0.4 mg/ml BSA, the telomerase extension substrate (TS, 200 nM HPLC purified 5'-AATCCGTCGAGCAGAGTT (SEQ ID NO: 5)), and 2.5 mM dNTPs. The extension was incubated at 25° C. for 40 mins followed by heat killing at 95° C. for 5 mins. The PCR reaction was performed in 1×EvaGreen ddPCR Supermix v2.0 (Bio-Rad) with 50 nM TS primer and 50 nM ACX reverse primer and 50 cell-equivalents of the extension reaction as input. Droplets were produced following the manufacturer's instructions in the droplet generator (Bio-Rad), and the emulsions were transferred to a 96-well plate for amplification (95° C. for 5 min, 40 cycles, 95° C. for 30 s, 54° C. for 30 s, 72° C. for 30 s, hold at 12° C.). Fluorescence was quantitated using a QX200 droplet reader (Bio-Rad) in the 6-Fam channel. Thresholds for quantitation were determined by comparison to a telomerase negative fibroblast cell line and no cell input negative control samples and untreated Hela cell positive control samples.

Parp Profiling.

Performed by BPS Bioscience Inc., San Diego by following the BPS PARP or TNKS assay kit protocols. The enzymatic reactions were conducted in duplicate at room temperature for 1 hr in a 96 well plate coated with histone substrate. 50 mL of reaction buffer (Tris.HCl, pH 8.0) contains $NAD^+$, biotinylated $NAD^+$, activated DNA, recombinant PARP enzyme and 10 µM of the test compound. Olaparib used at 20 nM concentration. After enzymatic reactions, 50 µL of Streptavidin-horseradish peroxidase was added to each well and the plate was incubated at room temperature for an additional 30 min. 100 µL of developer reagents were added to wells and luminescence was measured using a BioTek Synergy™ 2 microplate reader.

Example 2—Results of IWR-8 on Telomere Activity

From screening a 200K small molecule library in cells with autonomous Wnt signaling, ~60 compounds were identified that disrupted cellular response to Wnt ligands (termed Inhibitors of Wnt Response or IWR compounds) (Chen, et al., 2009). The identification of the Tnks enzymes as the target of two IWR compounds (IWR-1 and -2) suggested that other IWR compounds may also disable Wnt signaling by the same mechanism (Dodge and Lum, 2011; Huang and He, 2008). Inhibition of Tnks-mediated auto-parsylation, a biochemical trigger for its proteasome-mediated destruction, results in changes in Tnks abundance in cultured cells thus affording a straightforward screen for potentially novel Tnks inhibitors (FIG. 1A) (Huang, et al., 2009). The loss of β-catenin protein additionally serves as a useful marker of chemically induced Tnks inhibition. After subjecting all of the IWR compounds to these biochemical tests for Tnks inhibitory activity in cultured cells, six additional Tnks antagonists (IWR-3 to -8; FIG. 1B) were discovered. Thus, a total of four chemotypes supporting Tnks inhibition emerged from the inventors' original Wnt pathway antagonist screen (FIG. 1C). IWR-6 and -7 resemble the previously identified Tnks inhibitor XAV-939 whereas IWR-8 represents a unique chemotype with such activity.

Figures 2A, 2B, 2C:
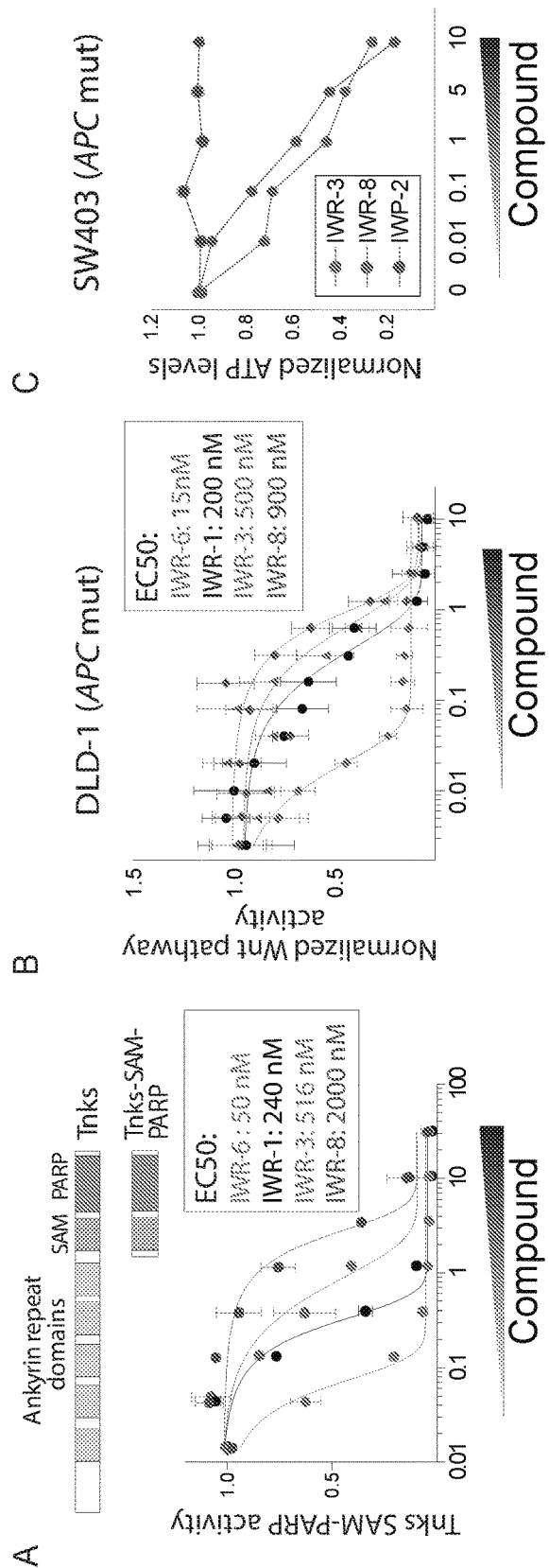
FIGS. 2A-2C show the novel Tnks inhibitor chemotype IWR-8 directly inhibits Tnks enzymes and disrupts β-catenin-dependent transcriptional activity induced by loss of APC function.

The molecules representative of each chemotype found in this chemical set were able to directly target Tnks using a recombinant Tnks protein assay that utilizes histone parsylation as a read out (FIG. 2A). Given the intense interest in developing Tnks inhibitors as anti-cancer drugs, the unique chemical scaffold supporting Tnks inhibition revealed by IWR-8 may provide new opportunities for achieving a drug-like molecule. Indeed, similar to other established Tnks inhibitors IWR-8 disrupted deviant Wnt signaling and cell growth in cells lacking normal APC activity in a dose-dependent fashion (FIGS. 2B-C). Thus, despite the absence of resemblance to other previously described Tnks inhibitors, IWR-8 exhibits both in vitro and in vivo activities associated with a bona fide Tnks inhibitor.

Tnks enzymes accommodate their ADP-ribose donor substrate, nicotinamide adenine dinucleotide (NAD+), in two sub-pockets—one binds the nicotinamide (NI) and another the adenosine (AD) moiety. IWR-1 was previously shown to be a first in class inhibitor that targets the AD-binding pocket rather than the NI binding pocket (Narwal, et al., 2012). The inventors' selected representative compounds from each group and determined their mode of attack using structural analyses. First, it was observed that IWR-1 engages the AD-binding pocket unlike prototypical PARP inhibitors represented here by the NI-binding pocket inhibitor XAV-939 (FIG. 3A, Table 1). IWR-2, a derivative of IWR-1, also binds Tnks1 in this mode (Gunaydin, et al., 2012). Despite their chemical dissimilarity, IWR-8 like IWR-1 exploits a histidine uniquely found in the D-loop of Tnks enzymes (His1201 in Tnks1; His1048 in Tnks2) to engage the AD pocket while concomitantly inducing a change in the D-loop conformation (FIG. 3B). Instead of a quinolone group found in IWR-1 that mediates aromatic stacking with His1201, IWR-8 achieves a similar chemical protein interaction using an indoline group. The crystallographic and NMR-based evidence suggests that the structure of IWR-8 is actually a regioisomer of the structure that was described in the first report of its synthesis shown in Example 4. Perhaps not surprising given its size, IWR-3 engages both NI- and AD-binding pockets (FIG. 3C). In the end, these Tnks antagonists can be organized based on their pocket binding preference (FIG. 3D).

TABLE 1

Data collection and refinement statistics for IWR compound/Tnks1 crystal structure

| Data collection | TNKS1/IWR1 | TNKS1/IWR3 | TNKS1/IWR8 |
|---|---|---|---|
| Space group | $P6_2$ | $P\,2_12_12_1$ | $P\,6_2$ |
| Cell dimensions | | | |
| a, b, c (Å) | 107.94, 107.94, 121.92 | 48.20, 81.17, 114.16 | 108.38, 108.38, 122.22 |
| α, β, γ (°) | 90, 90, 120 | 90, 90, 90 | 90, 90, 120 |
| Resolution (Å) | 50.0-2.3 (2.34-2.30)* | 31.0-1.8 (1.87-1.80) | 37.4-1.5 (1.55-1.50) |
| $R_{sym}$ | 11.2 (51.3) | 7.3 (>100) | 8.3 (95.1) |
| I/σI | 15.7 (2.4) | 38.8 (1.5) | 26.3 (1.3) |
| Completeness (%) | 99.7 (94.7) | 99.3 (94.5) | 99.1 (92.0) |
| Redundancy | 7.3 (5.2) | 7.0 (6.2) | 6.2 (3.0) |
| $CC_{1/2}$ at the highest resolution shell | 0.86 | 0.84 | 0.60 |
| Refinement | | | |
| Resolution (Å) | 2.30 | 1.80 | 1.50 |
| No. reflections | 34662 | 41860 | 128406 |
| Completeness (%) | 97 | 99 | 99 |
| $R_{work}/R_{free}$ (%) | 22.6/28.3 | 18.1/21.1 | 17.7/20.7 |
| No. atoms | 7048 | 3522 | 7804 |
| Protein | 6568 | 3262 | 6820 |
| Ligand/ion | 128 | 44 | 163 |
| Water | 352 | 216 | 821 |
| B-factors | | | |
| Protein | 43.7 | 45.7 | 22.0 |
| Ligand/ion | 40.6 | 37.3 | 26.2 |
| Water | 39.5 | 49.9 | 33.7 |
| R.m.s deviations | | | |
| Bond lengths (Å) | 0.004 | 0.007 | 0.007 |
| Bond angles (°) | 0.77 | 1.01 | 1.08 |
| Ramanchandran plot | | | |
| Favored (%) | 98.2 | 99.0 | 99.0 |
| Allowed (%) | 1.8 | 1.0 | 1.0 |
| Disallowed (%) | 0 | 0 | 0 |

*Highest resolution shell is shown in parenthesis.

The higher level of conservation between the NI-binding pocket in PARPs as compared to the AD-binding pocket likely imposes greater challenges to achieving specificity with NI-binding pocket inhibitors (Wahlberg, et al., 2012). Indeed the ~100-fold greater specificity of IWR-1 compared to XAV-939 for Tnks enzymes over several other PARPs has been attributed to their difference in their mode of attack (Narwal, et al., 2012; Gunaydin, et al., 2012). At the same time, the discovery of structurally distinct chemicals both capable of binding the AD-binding pocket in a similar fashion (IWR-1 and IWR-8) afforded an opportunity to evaluate the strength of this hypothesis. Two AD-binding pocket compounds (IWR-1 and IWR-8), one NI-binding pocket compound (IWR-6), and one dual pocket inhibitor (IWR-3) were profiled against a panel of recombinant PARP proteins that covers 70% of the protein family (Table 2). In support of the hypothesis, the AD-binding chemicals exhibited greater specificity than the NI-binding chemical. Surprisingly, despite having to engage both pockets, IWR-3 exhibited poor selectivity. In the end, the overall effort to glean novel Tnks antagonists from the inventors' IWR chemical collection identified two highly specific Tnks inhibitors—IWR-1 and IWR-8—with on-target activities confirmed using biochemical, structural, and cell biological analyses.

TABLE 2

Specificity of novel IWR Tnks inhibitors. Indicated IWR compounds (10 μM) and the control pan-PARP inhibitor Olaparib (20 nM) were incubated with indicated recombinant proteins and parsylation of immobilized histone measured

| | % inhibition | | | | |
|---|---|---|---|---|---|
| | AD pocket inhibitor | | NI pocket inhibitor | Dual pocket inhibitor | Control |
| | IWR-1 | IWR-8 | IWR-6 | IWR-3 | Olaparib |
| PARP1 | 0 | 0 | 44 | 0 | 100 |
| PARP2 | 5 | 3 | 71 | 27 | 100 |
| PARP3 | 6 | 11 | 60 | 11 | 100 |
| TNKS1 | 100 | 99 | 100 | 98 | N/A |
| TNKS2 | 100 | 99 | 100 | 100 | N/A |
| PARP6 | 0 | 0 | 0 | 6 | 100 |
| PARP7 | 7 | 8 | 9 | 20 | 87 |
| PARP8 | 1 | 0 | 0 | 21 | 96 |
| PARP10 | 18 | 9 | 8 | 49 | 99 |
| PARP11 | 2 | 12 | 32 | 17 | 96 |
| PARP12 | 11 | 14 | 36 | 31 | 84 |
| PARP15 | 0 | 0 | 0 | 28 | 82 |

Terf1 (also known as Trf1) is essential to telomere integrity by binding double stranded TTAGGG telomere repeats and is a well-established target of Tnks enzymatic activity (4). Each round of cell doubling engenders loss of some telomeric sequence due to the inability of the DNA replication machinery to achieve complete chromosomal end duplication (the "end replication" problem) (Palm and de Lange, et al., 2008). Loss of Terf1 has been shown to induce cohesion of telomere ends and the formation of G-quadruplexes in the lagging strand thus promoting telomere replication stalling and fragility (Zimmerman, et al., 2014). When telomeric sequences become sufficiently shortened, chromosomal ends become "uncapped" and are unable to properly engage the shelterin protective components such as Terf1 thereby resulting in a DNA damage response and cellular senescence or apoptosis. Cancerous cells overcome this cell growth braking mechanism largely by invoking telomerase expression (Shay and Wright, 2011).

Figures 4A, 4B, 4C, 4D, 4E, 4F:
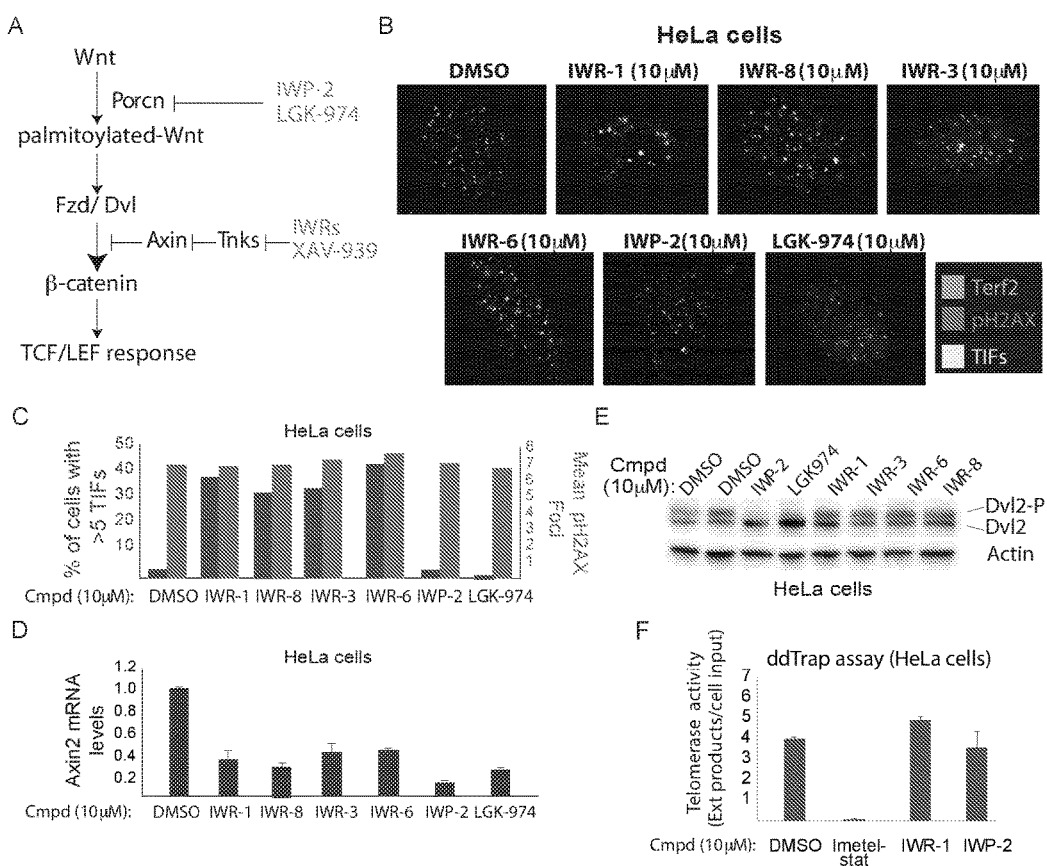
FIGS. 4A-4F show Tnks inhibitors induce telomeric stress in human cells independently of Wnt/β-catenin pathway inhibition.

The chemical dissimilarity of the IWR compounds was exploited to identify high confidence on-target effects of disrupting Tnks catalytic activity on telomere length maintenance. As controls, chemicals targeting Porcn, an acyl-transferase essential for Wnt-instructed β-catenin activation, were used as a means of influencing β-catenin without directly disabling Tnks (FIG. 4A). Telomere Induced Foci (TIF) are markers of telomeric damage scored by the appearance of co-localizing shelterin component Terf2/Trf2 and phosphorylated H2A.X (gamma H2A.X), a biochemical marker of damaged DNA (Takai, et al., 2003). Whereas the Tnks inhibitors markedly induced TIF formation in a cervical carcinoma cell line (HeLa cells), the Porcn inhibitors failed to do the same (FIGS. 4B-C). Yet, true to the previously assigned activities of Tnks and Porcn enzymes in Wnt signaling, all compounds tested disrupted the expression of Axing, a well-validated target gene of the Wnt/β-catenin pathway (FIG. 4D). At the same time, Porcn but not Tnks inhibitors blocked Wnt ligand dependent Frizzled receptor activity in these cells as measured by phosphorylation of the cytoplasmic signaling molecule Dishevelled 2 (Dvl2) (FIG. 4E) (Gonzalez-Sancho, et al., 2004: Jacob, et al., 2011). Finally, inadvertent direct inactivation of telomerase by Tnks inhibitors was ruled out as the cause of TIFs using IWR-1 in an in vitro assay for telomerase activity (FIG. 4F). Thus, the chemical induction of telomeric damage is independent of the effects stemming from the dampening of Wnt/β-catenin pathway activity.

Figures 5A, 5B, 5C, 5D, 5E:
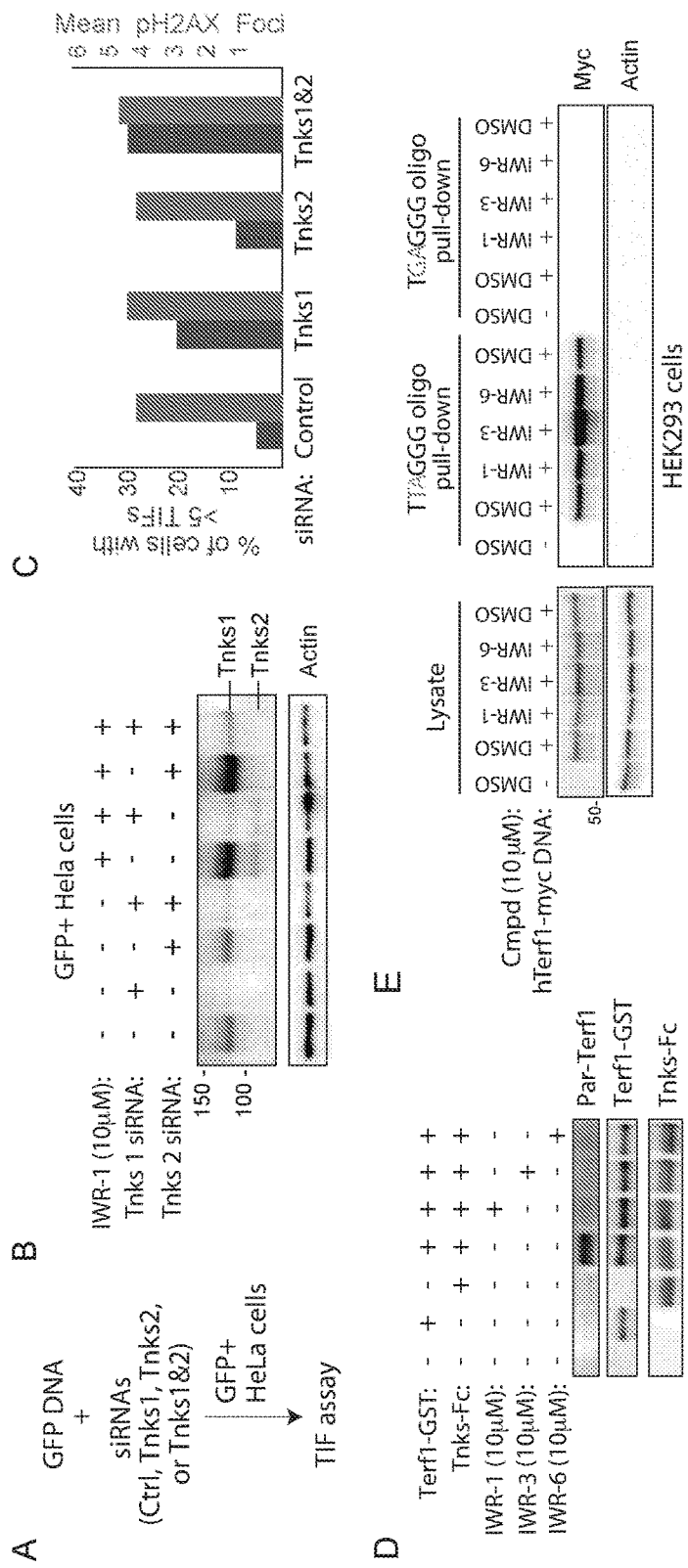
FIGS. 5A-5E show chemical disruption of Tnks likely results in increased parsylation-dependent Terf1 binding to telomeric DNA.

Using a cell sorting strategy to isolate cells transfected with pooled siRNAs targeting one or both Tnks transcripts (FIGS. 5A-B), using RNAi in HeLa cells demonstrrated that decreased Tnks1 and 2 protein is associated with an increased number of TIFs (FIG. 5C). Consistent with a previous report that both Tnks proteins contribute to Terf1 regulation, simultaneous knock-down of both transcripts gave rise to a greater induction of TIFs than from individual transcript targeting experiments (Cook, et al., 2002). Next, the effects of the IWR compounds on Tnks-mediated Terf1 parsylation using an in vitro reconstitution assay were directly evaluated. Three Tnks inhibitors with distinct chemotypes blocked Terf1 parsylation under these conditions thus providing evidence that both adenosine- and nicotinamide-binding pocket inhibitors likely disrupt Tnks regulation of Terf1 in cells (FIG. 5D).

Previous reports using overexpressed Tnks protein demonstrated changes in total Terf1 abundance upon increasing Tnks protein levels (Chang, et al., 2003; Seimiya, et al., 2005). In cells exposed to one of several IWR compounds, a change in total Terf1 was not detected which suggests that the majority of Terf1 protein is not subject to endogenous Tnks protein regulation (FIG. 5E). Nevertheless, a general increase in Terf1 binding to oligos with telomere repeat sequences was observed in cells treated with one of three IWR compounds tested (see FIG. 5E). These results are consistent with a previous report that Terf1 parsylation prevents its binding to telomeric DNA (Smith, et al., 1998). Notably, despite having the weakest anti-Tnks activity of the three IWR compounds evaluated, IWR-3 induced the greatest increase in Terf1 binding to telomeric repeat sequences (see FIGS. 2A-B). Given the promiscuity of IWR-3 for other PARP family members (see Table 2), without wishing to be bound by any theory, it is believed that other PARP family members may also participate in Terf1 regulation. Nevertheless, taking together the existing biochemical and genetic evidence that Tnks-Terf1 interaction is essential to telomere regulation, these observations demonstrate that IWR-dependent induction of TIFs is likely a consequence of impaired Tnks regulation of Terf1.

Figures 6A, 6B, 6C:
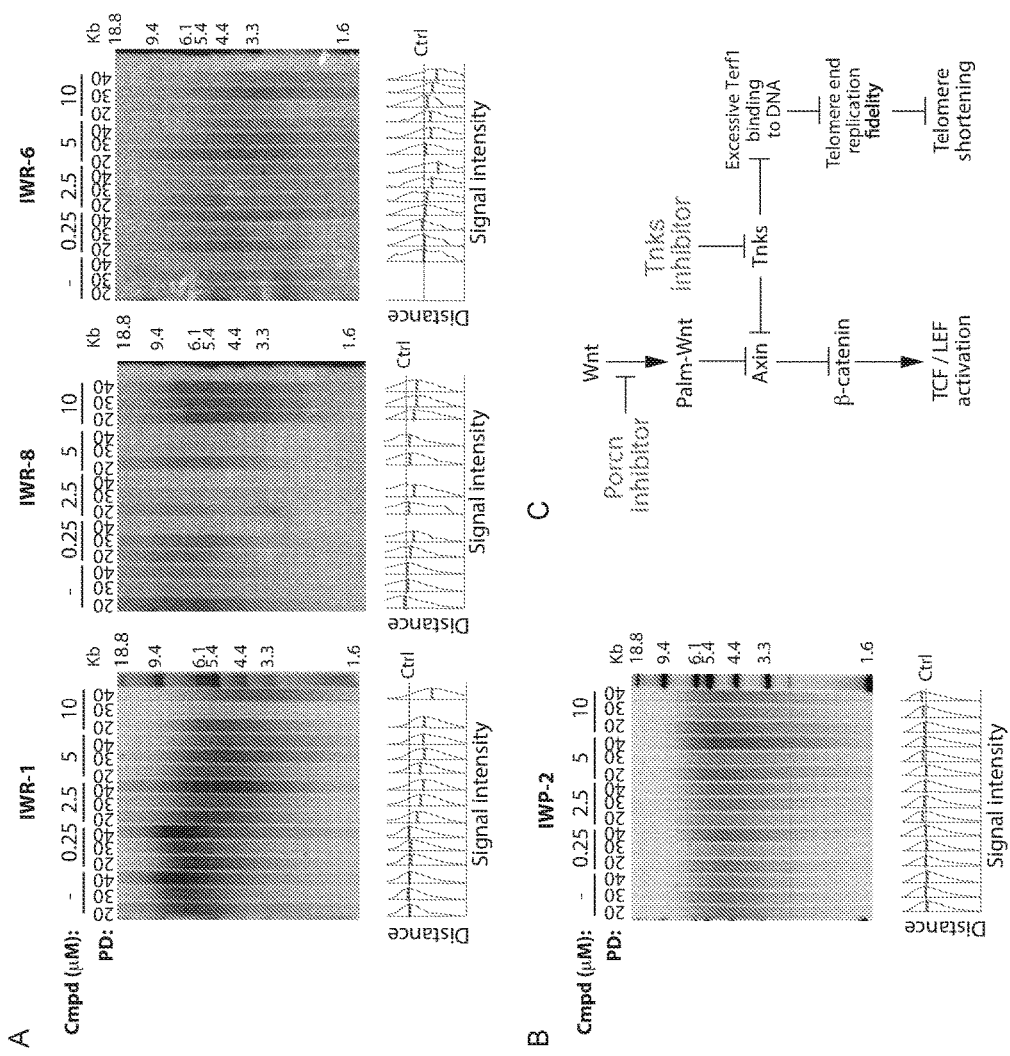
FIGS. 6A-6C show Tnks inhibitors but not a Porcn inhibitor induce telomeric shortening.

The effects of Tnks inhibition on telomere length maintenance in human HeLa cells treated for an extended period of time with IWR-1 (up to 40 population doublings) was evaluated. Whereas IWR-1, IWR-8 and IWR-6 induced shortened telomere length in a dose-dependent manner, the Porcn inhibitor IWP-2 did not (FIGS. 6A-B). This data is consistent with Tnks inhibitor-induced telomeric shortening independent of changes to Wnt signaling status in this cell line. Another study using XAV-939 observed similar effects on telomere length-maintenance in a neuroblastoma cell line thereby extending the relevance of the inventors' previous findings to other cell types (Tian, et al., 2014). Taken together, these findings reveal a single agent strategy for inducing telomerase shortening that is distinct from current efforts devoted to directly targeting telomerase. An inseparable biological impact on Wnt/β-catenin signaling and telomere length maintenance stemming from the chemical attack of Tnks enzymes was discovered (FIG. 6B).

Example 3—Discussion of Wnt Signaling and Tankyrase Enzyme Inhibition

Chemically based efforts to disable deviant Wnt/β-catenin signaling in cancer have converged on two major strategies that target either the Tnks or Porcn enzymes (Lum and Clevers, 2012). These findings reveal that suppression of telomere lengthening and Wnt/β-catenin signaling are coincident in cells treated with highly selective Tnks inhibitors. In the context of cancer, Tnks inhibitors may afford a single agent synthetic lethal strategy for targeting cancer initiating cells that rely on both cell sternness associated processes. At the same time, loss of Wnt/β-catenin signaling invoked by short or prolonged chemical attack of Porcn spares telomeres suggests that previous observations linking Wnt/β-catenin mediated transcription to telomere regulation may not be universal (Diala, et al., 2013; Hoffmeyer, et al., 2012; Zhang, et al., 2012) (see FIG. 6B).

Tnks and Porcn inhibitors including IWR-1 and IWP-2 are now widely used for the in vitro engineering of various tissues including cardiomyocytes, retinal pigmented epithelial cells, pneumocytes, and dopaminergic neurons (Ghaedi, et al., 2013; Huang, et al., 2014; Gonzalez, et al., 2011; Lian, et al., 2013; Nakano, et al., 2012; Narytnyk, et al., 2014; Ren, et al., 2011; Wang, et al., 2011). Given the transient nature of the chemical exposure in these protocols (typically 2-3 days) and similar efficacy of both Tnks and Porcn inhibitors for directing cell fate outcome in a direct comparison (Ren, et al., 2011), without wishing to be bound by any theory, it is believed that the chemical induction of these cells types is due to suppression of Wnt/β-catenin transcriptional responses and not telomeric stress or shortening. Further studies will be required to address whether or not concomitant induction of telomeric stress associated with the Tnks inhibition has any adverse affects on tissue engineering agendas.

The recent identification of specific Tnks inhibitors is timely given the development of Imetelstat, an oligonucleotide-based inhibitor representing the only small molecule targeting telomerase to advance in clinical testing, has stalled due to hematological and hepatoxic dose limiting side effects (Chen, 2008; Thompson, et al., 2013). Whereas PARP inhibitors have been posed to be useful for sensitizing telomeres for chemical attack using other agents (Seimiya, et al., 2005; Cerone, et al., 2011), these study using selective Tnks inhibitors suggest a single agent strategy can achieve the same endpoint. Moreover, the AD-binding pocket of Tnks can accommodate diverse pharmacophores as demonstrated here and from other efforts thus providing a more versatile starting point by comparison to Imetelstat with respect to medicinal chemistry goals (Haikarainen, et al., 2013). Recent advances in genetic testing have also uncovered new patient cohorts associated with long telomeric length that may benefit from a Tnks inhibitor including those with mutations in the shelterin component POT1 in familial melanoma and chronic lymphocytic leukemia (Ramsay, et al., 2013; Robles-Espinoza, et al., 2014; Shi, et al., 2014), the catalytic subunit of telomerase Tert in familial and sporadic melanoma (Horn, et al., 2013), and single nucleotide polymorphisms or mutations near the promoters for Tert in glioma and urothelial cancers (Borah, et al., 2015; Walsh, et al., 2014). Thus, the clinical development path for Tnks inhibitors as anti-cancer agents should not only include consideration of the status of Wnt/β-catenin signaling in various diseases but also the potential contribution of telomere-associated genetic alterations to drug sensitivity.

Example 4—Synthesis of IWR8

Compound 4. To a 25 mL vial charged with 2 (287 μL) and DCM (5 mL) was added 3 (229 mg), NEt$_3$ (697 μL), HOBt (270 mg) and EDCI (383 mg). Upon completion, the reaction was diluted with DCM, the organic layer was washed with 1 N HCl, water and dried over Na$_2$SO$_4$, filtered, concentrated and purified by HPLC to afford 4 (24 mg).

Compound 5. To a 4 mL vial charged with 4 (12 mg) was added 20% TFA in DCM (0.4 mL). Upon completion, the solvent was removed, the residue was dissolved in EA, the organic layer was washed with sat. NaHCO$_3$, dried over Na$_2$SO$_4$, filtered and concentrated to afford 5 (6.2 mg).

Compound 7. To a 4 ml vial charged with 6 (200 mg) was added ClSO$_3$H (200 μL). After stirring at 70° C. for 2 d, the reaction was quenched by adding into ice-cold water slowly. The so lid was washed with H$_2$O, filtered and dried under vacuum to afford a mixture of 6 and 7 (170 mg) (6/7=½). $^1$H NMR (400 M Hz, CDCl$_3$) δ 8.99 (s, 1H), 7.60 (s, 1H), 4.17 (t, J=8.6 Hz, 2H), 3.31 (t, J=8.6 Hz, 2H), 2.25 (s, 3H). $^{13}$C NMR (100 MHz, CDCl$_3$) δ 169.2, 143.0, 142.2, 140.1, 132.0, 118.3, 114.2, 49.0, 27.9, 24.2.

IWR8 (8). To a 4 mL vial charged with 5 (6.2 mg) obtained above and DCM (0.5 ml) was added pyridine (12.1 μL), a mixture of 6 and 7 (25.4 mg) and DMAP (3.0 mg). Upon completion, the reaction was diluted with EA, the organic layer was washed with 0.5 N HCl, water and dried over Na$_2$SO$_4$, filtered and concentrated, the residue was purified by HPLC to afford IWR8 (8) (4.1 mg). $^1$H NMR (400 M Hz, CDCl$_3$) δ 8.7 4 (s, 1H), 7.45 (s, 1H), 7.27 (t, J=7.6 Hz, 1H), 7.15 (d, J=7.5 Hz, 1H), 6.93-6.84 (m, 2H), 4.09 (t, J=8.4 Hz, 2H), 3.75 (d, J=11.9 Hz, 2H), 3.66 (q, J=7.1 Hz, 2H), 3.21 (t, J=8.4 Hz, 2H), 2.54 (t, J=12.3 Hz, 2H), 2.36 (s, 3H), 2.25-2.15 (m, 1H), 2.20 (s, 3H), 1.89-1.73 (m, 2H), 1.65-1.55 (m, 2H), 1.05 (t, J=7.1 Hz, 3H).

Synthesis scheme:

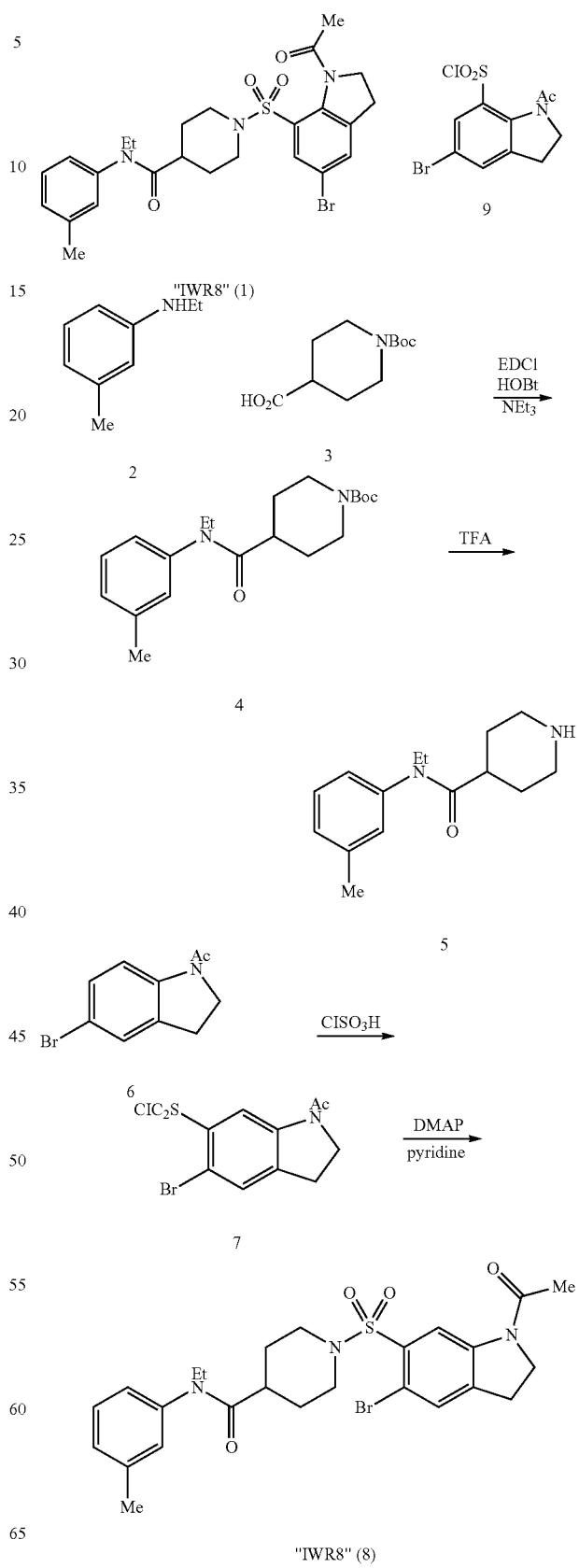

The procedure reported by ChemDiv (Dorogov, et al., 2004) was used to synthesize the presumed structure of IWR8 (1) that was originally purchased from ChemDiv (scheme). While $^1$H NMR spectrum of the final product is the same as that of the library compound, crystallographic studies indicate that the correct structure of IWR8 is 8 instead of 1. The $^1$H—$^1$H COSY, $^1$H—$^{13}$C HSQC, and $^1$H—$^{13}$C HMBC studies also support that sulfonylation of 6 gave 7 but not 9, consistent with the findings reported by Herchen, Petersen, and co-workers (Borrow, et al., 1988).

All of the methods and apparatuses disclosed and claimed herein can be made and executed without undue experimentation in light of the present disclosure. While the compositions and methods of this invention have been described in terms of preferred embodiments, it will be apparent to those of skill in the art that variations may be applied to the methods and apparatuses and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,843,063
U.S. Pat. No. 5,641,747
U.S. Pat. No. 5,777,193
U.S. Pat. No. 5,806,529
U.S. Pat. No. 6,686,148
U.S. Pat. No. 6,699,873
U.S. Pat. No. 6,833,354
U.S. Pat. No. 6,943,151
U.S. Pat. No. 7,186,683
U.S. Pat. No. 7,241,732
U.S. Pat. No. RE35,694
U.S. Provisional Patent Appln. 61/130,149
Abrami et al., *Proc. Natl. Acad. Sci. USA,* 105(14):5384-53849, 2008.
Adams *Acta crystallographica. Section D, Biological crystallography,* 58:1948-1954, 2002.
Ailles and Weissman, *Curr. Opin. Biotech.,* 18:460-466, 2007.
Barker and Clevers, *Nat. Rev. Drug Discov.,* 5:997-1014, 2006.
Barker, et al., *Nature,* 457(7229):608-611, 2009.
Barton-Davis et al., *Proc. Natl. Acad. Sci. USA,* 95:15603, 1998.
Bilic et al., *Science,* 316:1619-1622, 2007.
Borah, et al., *Science,* 347:1006-1010, 2015.
Borror, et al., *J. Org. Chem.,* 53:2047-2052.
Brack et al., *Science,* 317:807-810, 2007.
Cadigan and Waterman, *Cold Spring Harbor perspectives in biology,* 4(11), 2012.
Cerone et al., *Cancer Res.,* 71:3328-3340, 2011.
Chang et al., *Genes Dev,* 17:1328-1333, 2003.
Chang et al., *The Biochemical journal,* 391:177-184, 2005.
Chen et al., *Acta crystallographica. Section D, Biological crystallography,* 66:12-21, 2010.
Chen et al., *Nat. Chem. Biol.,* 5:100-107 2009.
Chen et al., *Oncogene,* 27:3483-3488, 2008.
Chen, et al., *Nat Chem Biol,* 5:100-107, 2009.
Chiang, et al., *PLoS ONE,* 3:e2639, 2008.
Cho-Park and Steller *Cell,* 153:614-627, 2013.
Clevers, *Cell,* 127:469-480, 2006.
Cole et al., *Genes Dev.,* 22:746-755, 2008.
Cook, *Mol Cell Biol.,* 22:332-342, 2002.
Diala et al., *EMBO reports,* 14:356-363, 2013.
Distler, et al., *Annals of the rheumatic diseases,* 72(9):1575-1580, 2013.
Dodge and Lum, *Annu Rev Pharmacol Toxicol,* 51:289-310, 2011.
Dorogov, et al., *Synthesis,* 18:2999-3004.
Emsley and Cowtan, *Acta crystallographica. Section D, Biological crystallography,* 60:2126-2132, 2004.
Fearon and Vogelstein, *Cell,* 61(5):759-767, 1990.
Fevr et al., *Mol. Cell Biol.,* 27:7551-7559, 2007.
Ghaedi et al., *J Clin Invest.,* 123:4950-4962, 2013.
Gonzalez et al., *Angew Chem Int Ed Engl.,* 50:11181-11185, 2011.
Gonzalez-Sancho, et al., *Mol Cell Biol.,* 24:4757-4768, 2004.
Greene and Wuts, In: *Protective Groups in Organic Synthesis,* 2$^{nd}$ Ed.; Wiley, N.Y., 1999.
Guettler, et al., *Cell,* 147:1340-1354, 2011.
Gunaydin et al., *PLoS ONE,* 7:e33740, 2012.
Haikarainen, et al., *PLoS ONE,* 8: e65404, 2013.
Handbook of Pharmaceutical Salts: Properties, Selection and Use, 2002.
Hayashi et al., *Nature structural & molecular biology,* 19:387-394, 2012.
Henderson, et al., *Proc Natl Acad Sci USA,* 107(32):14309-14314, 2010.
Hoffmeyer et al., *Science,* 336:1549-1554, 2012.
Horn et al., *Science,* 339:959-961, 2013.
Huang and He, *Curr. Opin. Cell Biol.,* 20(2):119-125, 2008.
Huang and He, *Current opinion in cell biology,* 2008.
Huang et al., *Nature biotechnology,* 32:84-91, 2014.
Huang et al., *Nature,* 461:614-620, 2009.
Jacob et al., *Science signaling,* 4:ra4, 2011.
Kim and Smith, *Molecular biology of the cell,* 25:30-40, 2014.
Kinzler and Vogelstein, *Cell,* 87:159-170, 1996.
Korinek et al., *Nat. Genet.,* 19:379-383, 1998.
Kurayoshi et al., *Biochem. J.,* 402:515, 2007.
Lee et al., *PLoS Biol.,* 1:E10, 2003; erratum in *PLoS Biol.,* 2:E89 (2004).
Lehtio et al., *FEBS J.,* 280:3576-3593, 2013.
Lehtio, et al., *Journal of molecular biology,* 379:136-145, 2008.
Lian et al., *Nature protocols,* 8:162-175, 2013.
Lian, et al., *Nature protocols,* 8(4162-175, 2013.
Liu et al., *Science,* 317:803-806, 2007.
Lu et al., *Bioorg. Med. Chem. Lett.,* Apr. 18, 2009 (Epub ahead of print).
Ludlow, et al., *Nucleic Acids Res.,* 2014.
Lum and Clevers *Science,* 337:922-923, 2012.
Lum, et al., *The Journal of biological chemistry,* 273:26236-26247, 1998.
Lynch, *Exp. Opin. Emerging Drugs,* 9:345, 2004.
March's Advanced Organic Chemistry: Reactions, Mechanisms, and Structure (March's Advanced Organic Chemistry), Smith and March (Eds.), 2001.
McCoy, et al., *Journal of applied crystallography,* 40:658-674, 2007.
Muncan et al., *EMBO Rpts.,* 8:966-973, 2007.

Munoz et al., *Mol. Cell Biol.*, 29:1608-1625, 2009.
Nakano, et al., *Cell stem cell* 10:771-785, 2012.
Nakano, et al., *Cell stem cell*, 10(6):771-785, 2012.
Narwal et al., *Journal of medicinal chemistry*, 55:1360-1367, 2012.
Narytnyk, et al., *Stem cell reviews*, 10(2):316-326, 2014.
Narytnyk, et al., *Stem cell reviews*, 10:316-326, 2014.
Ohki and Ishikawa, *Nucleic Acids Res.*, 32:1627-1637, 2004.
Orsulic et al., *J. Cell Sci.*, 112 (Pt 8):1237-1245, 1999.
Ozaki et al., *Mol Cell*, 47:694-706, 2012.
Palm and de Lange, *Annual review of genetics*, 42:301-334, 2008.
Polakis, *Curr. Opin. Genet. Develop.*, 17:45-51, 2007.
Ramsay, et al., *Nat Genet.*, 45:526-530, 2013.
Remington's Pharmaceutical Sciences, 18th Ed. Mack Printing Company, 1289-1329, 1990.
Ren et al., *J Mol Cell Cardiol.* 51:280-287, 2011.
Ren, et al., *J Mol Cell Cardiol*, 51(3):280-287, 2011.
Reya and Clevers, *Nature*, 434:843-850, 2005.
Riffell et al., *Nat Rev Drug Discov.*, 11:923-936, 2012.
Robles-Espinoza et al., *Nat Genet.*, 46:478-481, 2014.
Sarek et al., *Mol Cell*, 57:622-635, 2015.
Scholer-Dahirel, et al., *Proc. Natl. Acad. Sci., USA.*, 2011.
Schwarz-Romond et al., *J. Cell Sci.*, 120:2402-2412, 2007.
Seimiya et al., *Cancer Cell*, 7:25-37, 2005.
Shay and Wright *Seminars in cancer biology*, 21:349-353, 2011.
Shepard et al., *Proc. Natl. Acad. Sci. USA*, 102:13194-13199, 2005.
Shi, et al., *Nat. Genet.*, 46:482-486, 2014.
Sjoblom et al., *Science*, 314:268-274, 2006.
Smith et al., *Science*, 282:1484-1487, 1998.
Stoick-Cooper et al., *Development*, 134:479-489, 2007.
Takada et al., *Dev. Cell*, 11:791-801, 2006.
Takai et al. *Curr Biol.*, 13:1549-1556, 2003.
The Cancer Genome Atlas Network, *Nature*, 487(7407):330-337, 2012.
Thompson, et al., *Clin Cancer Res.*, 19:6578-6584, 2013.
Tian et al., *Oncology reports*, 32:1999-2006, 2014.
Van der Flier et al., *Gastroenterology*, 132:628-632, 2007.
Veeman et al., *Developmental Cell*, 5:367, 2003.
Wahlberg, et al., *Nature biotechnology*, 30:283-288, 2012.
Walsh, et al., *Nat. Genet.*, 46:731-735, 2014.
Wang et al., *ACS chemical biology*, 6:192-197, 2011.
Wang, et al., *American journal of physiology. Cell physiology*, 307(3):C234-244, 2014.
Wang, et al., *Science*, 327(5973):1650-1653.
Yang, et al., *Hepatology*, 60(3):964-976, 2014.
Zhang et al., *The Journal of biological chemistry*, 287: 32494-32511, 2012.
Zimmermann et al., *Genes Dev*, 28:2477-2491, 2014.

What is claimed is:

1. A method of inhibiting a Tankyrase enzyme in a cell comprising administering to the cell an amount sufficient to cause inhibition of a compound of the formula:

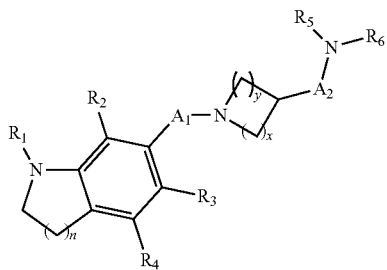

(I)

wherein:
- $R_1$ is hydrogen, alkyl$_{(C \leq 8)}$, substituted alkyl$_{(C \leq 8)}$, acyl$_{(C \leq 8)}$, or substituted acyl$_{(C \leq 8)}$;
- $R_2$, $R_3$, and $R_4$ are each independently selected from hydrogen, amino, cyano, halo, hydroxy, nitro, alkyl$_{(C \leq 8)}$, substituted alkyl$_{(C \leq 8)}$, alkoxy$_{(C \leq 8)}$, substituted alkoxy$_{(C \leq 8)}$, alkylamino$_{(C \leq 8)}$, substituted alkylamino$_{(C \leq 8)}$, dialkylamino$_{(C \leq 8)}$, substituted dialkylamino$_{(C \leq 8)}$, amido$_{(C \leq 8)}$, substituted amido$_{(C \leq 8)}$, acyl$_{(C \leq 8)}$, or substituted acyl$_{(C \leq 8)}$;
- n is 1, 2, 3, or 4;
- $A_1$ and $A_2$ are each independently selected from —C(O)— or —S(O)$_2$—;
- x and y are each independently selected from 1, 2, 3, 4, or 5;
- $R_5$ is hydrogen, alkyl$_{(C \leq 8)}$, substituted alkyl$_{(C \leq 8)}$, acyl$_{(C \leq 8)}$, or substituted acyl$_{(C \leq 8)}$;
- $R_6$ is aryl$_{(C \leq 12)}$, heteroaryl$_{(C \leq 12)}$, or a substituted version of either of these groups;

or a pharmaceutically acceptable salt thereof.

2. The method of claim 1, wherein $R_1$ is acyl$_{(C \leq 8)}$ or substituted acyl$_{(C \leq 8)}$.

3. The method of claim 1, wherein n is 1 or 2.

4. The method of claim 1, wherein $R_2$ is halo.

5. The method of claim 1, wherein x and y are 1 or 2.

6. The method of claim 1, wherein $R_5$ is alkyl$_{(C \leq 8)}$ or substituted alkyl$_{(C \leq 8)}$.

7. The method of claim 1, wherein $R_6$ is aryl$_{(C \leq 12)}$ or substituted aryl$_{(C \leq 12)}$.

8. The method of claim 7, wherein $R_6$ is tolyl.

9. The method of claim 7, wherein $R_6$ is 3-methylphenyl.

10. The method of claim 1, wherein the compound is further defined as:

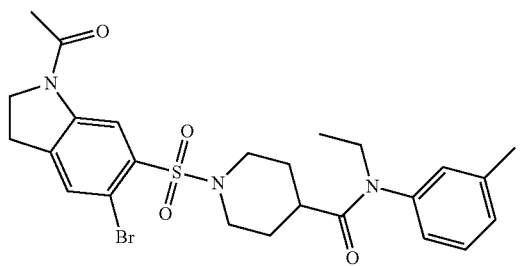 [SMILES: CCN(C(=O)C1CCN(S(=O)(=O)c2cc3c(cc2Br)CCN3C(C)=O)CC1)c1cccc(C)c1]

or a pharmaceutically acceptable salt thereof.

11. The method of claim 1, wherein the Tankyrase enzyme is Tankyrase 1.

12. The method of claim 1, wherein the Tankyrase enzyme is Tankyrase 2.

13. The method of claim 1 further comprising adding one or more additional inhibitors of a Tankyrase enzyme.

14. A method of treating a disease or disorder associated with the misregulation of a Tankyrase enzyme in a patient comprising administering to the patient in need thereof a therapeutically effective amount of a compound or a pharmaceutical composition comprising a compound of the formula:

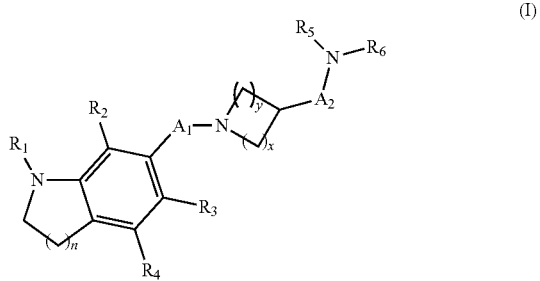

(I)

wherein:
- $R_1$ is hydrogen, alkyl$_{(C \leq 8)}$, substituted alkyl$_{(C \leq 8)}$, acyl$_{(C \leq 8)}$, or substituted acyl$_{(C \leq 8)}$;
- $R_2$, $R_3$, and $R_4$ are each independently selected from hydrogen, amino, cyano, halo, hydroxy, nitro, alkyl$_{(C \leq 8)}$, substituted alkyl$_{(C \leq 8)}$, alkoxy$_{(C \leq 8)}$, substituted alkoxy$_{(C \leq 8)}$, alkylamino$_{(C \leq 8)}$, substituted alkylamino$_{(C \leq 8)}$, dialkylamino$_{(C \leq 8)}$, substituted dialkylamino$_{(C≤8)}$, amido$_{(C≤8)}$, substituted amido$_{(C≤8)}$, acyl$_{(C≤8)}$, or substituted acyl$_{(C≤8)}$;

n is 1, 2, 3, or 4;

$A_1$ and $A_2$ are each independently selected from —C(O)— or —S(O)$_2$—;

x and y are each independently selected from 1, 2, 3, 4, or 5;

$R_5$ is hydrogen, alkyl$_{(C≤8)}$, substituted alkyl$_{(C≤8)}$, acyl$_{(C≤8)}$, or substituted acyl$_{(C≤8)}$;

$R_6$ is aryl$_{(C≤12)}$, heteroaryl$_{(C≤12)}$, or a substituted version of either of these groups;

or a pharmaceutically acceptable salt thereof.

15. The method of claim 14, wherein the compound is further defined as:

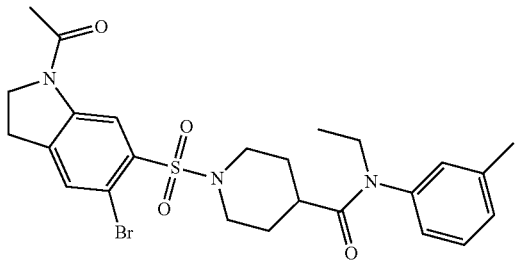 [SMILES: CCN(C(=O)C1CCN(S(=O)(=O)c2cc3c(cc2Br)CCN3C(C)=O)CC1)c1cccc(C)c1]

or a pharmaceutically acceptable salt thereof.

16. A pharmaceutical composition comprising an excipient or a pharmaceutically acceptable carrier and a compound of the formula:

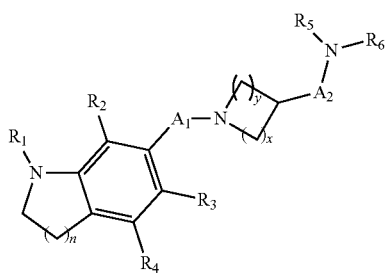

(I)

wherein:

$R_1$ is hydrogen, alkyl$_{(C≤8)}$, substituted alkyl$_{(C≤8)}$, acyl$_{(C≤8)}$, or substituted acyl$_{(C≤8)}$;

$R_2$, $R_3$, and $R_4$ are each independently selected from hydrogen, amino, cyano, halo, hydroxy, nitro, alkyl$_{(C≤8)}$, substituted alkyl$_{(C≤8)}$, alkoxy$_{(C≤8)}$, substituted alkoxy$_{(C≤8)}$, alkylamino$_{(C≤8)}$, substituted alkylamino$_{(C≤8)}$, dialkylamino$_{(C≤8)}$, substituted dialkylamino$_{(C≤8)}$, amido$_{(C≤8)}$, substituted amido$_{(C≤8)}$, acyl$_{(C≤8)}$, or substituted acyl$_{(C≤8)}$;

n is 1, 2, 3, or 4;

$A_1$ and $A_2$ are each independently selected from —C(O)— or —S(O)$_2$—;

x and y are each independently selected from 1, 2, 3, 4, or 5;

$R_5$ is hydrogen, alkyl$_{(C≤8)}$, substituted alkyl$_{(C≤8)}$, acyl$_{(C≤8)}$, or substituted acyl$_{(C≤8)}$;

$R_6$ is aryl$_{(C≤12)}$, heteroaryl$_{(C≤12)}$, or a substituted version of either of these groups;

or a pharmaceutically acceptable salt thereof.

17. The pharmaceutical composition of claim 16, wherein the compound is further defined as:

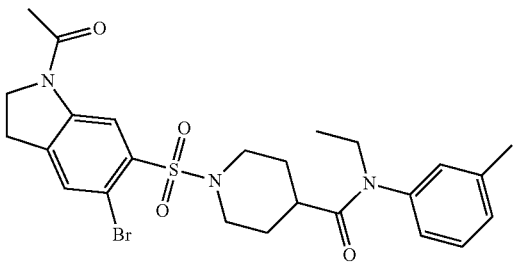 [SMILES: CCN(C(=O)C1CCN(S(=O)(=O)c2cc3c(cc2Br)CCN3C(C)=O)CC1)c1cccc(C)c1]

or a pharmaceutically acceptable salt thereof.

* * * * *